(12) United States Patent
Samaritani et al.

(10) Patent No.: US 7,741,268 B2
(45) Date of Patent: Jun. 22, 2010

(54) LIQUID PHARMACEUTICAL FORMULATIONS OF FSH AND LH TOGETHER WITH A NON-IONIC SURFACTANT

(75) Inventors: Fabrizio Samaritani, Rome (IT); Piergiorgio Donati, Morges (CH)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 10/551,840

(22) PCT Filed: Apr. 2, 2004

(86) PCT No.: PCT/EP2004/050432

§ 371 (c)(1),
(2), (4) Date: Jan. 20, 2006

(87) PCT Pub. No.: WO2004/087213

PCT Pub. Date: Oct. 14, 2004

(65) Prior Publication Data

US 2006/0147480 A1    Jul. 6, 2006

(30) Foreign Application Priority Data

Apr. 2, 2003  (EP) ................................... 03100882
May 27, 2003 (EP) ................................... 03101543
Jun. 20, 2003 (EP) ................................... 03101828

(51) Int. Cl.
*A61K 38/24* (2006.01)
(52) U.S. Cl. .......................................... 514/2; 530/313
(58) Field of Classification Search ...................... None
See application file for complete search history.

(56) References Cited

U.S. PATENT DOCUMENTS

| | | | |
|---|---|---|---|
| 4,496,537 A | 1/1985 | Kwan | |
| 4,589,402 A | 5/1986 | Hodgen et al. | |
| 4,659,696 A | 4/1987 | Hirai et al. | |
| 4,670,419 A | 6/1987 | Uda et al. | |
| 4,746,508 A | 5/1988 | Carey et al. | |
| 4,839,341 A | 6/1989 | Massey | |
| 4,962,091 A | 10/1990 | Eppstein et al. | |
| 5,087,615 A | 2/1992 | Chappel et al. | |
| 5,128,453 A | 7/1992 | Arpaia et al. | |
| 5,162,306 A | 11/1992 | Donaldson | |
| 5,270,057 A | 12/1993 | de Meere et al. | |
| 5,356,876 A | 10/1994 | Espey | |
| 5,374,620 A | 12/1994 | Clark et al. | |
| 5,384,132 A | 1/1995 | De Meere et al. | |
| 5,508,261 A | 4/1996 | Moyle et al. | |
| 5,580,856 A | 12/1996 | Prestrelski et al. | |
| 5,639,640 A | 6/1997 | Reddy et al. | |
| 5,650,390 A | 7/1997 | Samaritani et al. | |
| 5,661,125 A | 8/1997 | Strickland | |
| 5,681,822 A | 10/1997 | Bornstein et al. | |
| 5,733,572 A | 3/1998 | Unger et al. | |
| 5,767,067 A | 6/1998 | Arpaia et al. | |
| 5,811,096 A | 9/1998 | Aleman et al. | |
| 5,889,110 A | 3/1999 | Hutchinson et al. | |
| 5,929,028 A * | 7/1999 | Skrabanja et al. ............... 514/2 |
| 5,945,187 A | 8/1999 | Buch-Rasmussen et al. | |
| 6,066,620 A | 5/2000 | McGregor et al. | |
| 6,113,947 A * | 9/2000 | Cleland et al. ............... 424/489 |
| 6,136,784 A | 10/2000 | L'Italien et al. | |
| 6,238,890 B1 | 5/2001 | Boime et al. | |
| 6,267,958 B1 | 7/2001 | Andya et al. | |
| 6,346,274 B1 * | 2/2002 | Koll et al. .................... 424/497 |
| 6,440,930 B1 | 8/2002 | Rinella, Jr. | |
| 6,524,557 B1 * | 2/2003 | Backstrom et al. ............ 424/46 |
| 6,541,606 B2 | 4/2003 | Margolin et al. | |
| 6,573,237 B2 | 6/2003 | Rinella, Jr. | |
| 2002/0165146 A1 * | 11/2002 | Hoffman et al. ............... 514/12 |
| 2003/0072803 A1 | 4/2003 | Goldenberg et al. | |
| 2004/0028733 A1 | 2/2004 | Tracy et al. | |

FOREIGN PATENT DOCUMENTS

| | | |
|---|---|---|
| CA | 1340132 | 11/1998 |
| DE | 41 17 078 A1 | 11/1882 |
| EP | 0 318 081 | 5/1989 |
| EP | 0 448 146 | 9/1991 |
| EP | 0 652 766 | 7/1993 |
| EP | 0 603 159 | 6/1994 |
| EP | 0 853 945 | 7/1998 |
| EP | 0 920 873 | 12/1998 |
| EP | 0 891 774 | 1/1999 |

(Continued)

OTHER PUBLICATIONS

U.S. Appl. No. 10/561,529, filed Dec. 20, 2005, Samaritani et al.

(Continued)

*Primary Examiner*—Anish Gupta
(74) *Attorney, Agent, or Firm*—Woodard Emhardt Moriarty McNett & Henry

(57) ABSTRACT

The invention relates to the field of pharmaceutical formulations of follicle-stimulating hormone (FSH), luteinising hormone (LH), and mixtures of FSH and luteinising hormone (LH), and to methods of producing such formulations. The invention provides a liquid or freeze-dried formulation of FSH, or LH, or FSH and LH comprising a surfactant selected from Pluronic® F77, Pluronic F87, Pluronic F88 and Pluronic F68.

58 Claims, 1 Drawing Sheet

FOREIGN PATENT DOCUMENTS

| | | |
|---|---|---|
| EP | 0 668 073 | 4/1999 |
| EP | 1 191 099 | 6/1999 |
| EP | 0 736 303 | 8/1999 |
| EP | 0 974 359 | 1/2000 |
| EP | 0974359 * | 1/2000 |
| FR | 2 782 455 | 2/2000 |
| FR | 2782455 | 2/2000 |
| GB | 839300 | 8/1958 |
| GB | 1 065 127 | 4/1967 |
| GB | 1065127 | 4/1967 |
| WO | WO 92/21332 | 12/1992 |
| WO | WO 92/22568 | 12/1992 |
| WO | WO 93/11788 | 6/1993 |
| WO | WO 94/03198 | 2/1994 |
| WO | WO 97/04801 | 2/1997 |
| WO | WO 97/17087 | 5/1997 |
| WO | WO 98/30592 | 7/1998 |
| WO | 99 21534 | 5/1999 |
| WO | WO 99/21534 | 5/1999 |

OTHER PUBLICATIONS

Wenzel et al. "Pluronic F127 gel formulations of Deslorelin and GnRH reduce drug degradation and sustain drug release and effect in cattle", Journal of Controlled Release, vol. 85, pp. 51-59 2002.

Newman et al. "Use of Nonionic Block Copolymers in Vaccines and Therapeutics", Critical Reviews in Therapeutic Drug Carrier Systems, vol. 15, No. 2, pp. 89-140 1998.

Burgues et al. "Subcutaneous self-administration of highly purified follicle stimulating hormone and human chorionic gonadotrophin for the treatment of male hypogonadotrophic hypogonadism", Human Reproduction, vol. 12, No. 5, pp. 980-986 1997.

Shome et al. "A Reevaluation of the Amino Acid Sequence of Human Follitropin beta-Subunit", Journal of Protein Chemistry, vol. 7, No. 4, pp. 325-339 1988.

Keutmann et al. "Structure of Human Luteinizing Hormone Beta Subunit: Evidence for a Related Carboxyl-Terminal Sequence Among Certain Peptide Hormones", Biochemical and Biophysical Research Communications, vol. 90, No. 3, pp. 842-848 1979.

Talmadge et al. "Evolution of the genes for the beta subunits of human chorionic gonadotropin and luteinizing hormone", Nature, vol. 307, pp. 37-40 1984.

Fiddes et al. "Structure, Expression, and Evolution of the Genes for the Human Glycoprotein Hormones", Recent Progress in Hormone Research, vol. 40, pp. 43-78.

Klein et al. "Pharmacokinetics and pharmacodynamics of single-chain recombinant human follicle-stimulating hormone containing the human chorionic gonadotropin carboxyterminal peptide in the rhesus monkey", Fertility and Sterility, vol. 77, No. 6, pp. 1248-1255 2002.

Fiddes et al. "The Gene Encoding the Common Alpha Subunit of the Four Human Glycoprotein Hormones", Journal of Molecular and Applied Genetics, vol. 1, pp. 3-18 1981.

Maurer et al. "Isolation and Nucleotide Sequence Analysis of a Cloned cDNA Encoding the beta-Subunit of Bovine Follicle-Stimulating Hormone", DNA, vol. 5, No. 5, pp. 363-369 1986.

Watkins et al. "DNA Sequence and Regional Assignment of the Human Follicle-Stimulating Hormone beta-Subunit Gene to the Short Arm of Human Chromosome 11", DNA, vol. 6, No. 3, pp. 205-212 1987.

Hirai et al. "The gene for the beta subunit of porcine FSH: absence of consensus oestrogen-responsive element and presence of retroposons", Journal of Molecular Endocrinology, vol. 5, pp. 147-158 1990.

Maurer. "Molecular Cloning and Nucleotide Sequence Analysis of Complementary Deoxyribonucleic Acid for the beta-Subunit of Rat Follicle Stimulating Hormone", Molecular Endocrinology, vol. 1, pp. 717-723 1987.

Guzman et al. "The Gene Encoding Ovine Follicle-Stimulating Hormone beta: Isolation, Characterization, and Comparison to a Related Ovine Genomic Sequence", DNA and Cell Biology, vol. 10, No. 8, pp. 593-601 1991.

Kumar et al. "Cloning of the mouse gonadotropin beta-subunit-encoding genes, II. Structure of the luteinizing hormone beta-subunit-encoding genes", Gene, vol. 166, pp. 335-336 1995.

Kumar et al. "Cloning of the mouse gonadotropin beta-subunit-encoding genes, I. Structure of the follicle-stimulating hormone beta-subunit-encoding gene", Gene, vol. 166, pp. 333-334 1995.

Steelman et al. "Assay of the Follicle Stimulating Hormone Based on the Augmentation with Human Chorionic Gonadotropin", Endocrinology, vol. 53, pp. 604-616 1953.

Van Hell et al. "Effects of Human Menopausal Gonadotrophin Preparations in Different Bioassay Methods", Acta Endocrinologica, vol. 47, pp. 409-418 1964.

Akers Michael J., "Considerations in selecting antimicrobial preservative agents for parenteral product development", Pharmaceutical Technology, May 1984, pp. 36-46.

Akers, Michael J., "Excipient—Drug Interactions in Parenteral Formulations", Journal of Pharmaceutical Sciences, Nov. 2002, vol. 91, No. 11, pp. 2283-2300.

Amir, Syed M. et al., "Phenol, A Potent Stimulator of Adenylate Cyclase in Human Thyroid Membranes", Endocrine Research Communications, 8(2):83-95, 1981.

A.P.L.® Injection 5 000 IU and Injection 10 000 IU, http://home.intekom.com/pharm/akromed/apl-inj.html, Dec. 12, 2002, pp. 1-2.

A.P.L.® (chorionic gonadotropin for injection, USP), for Intramuscular Injection Only, Physicians' Desk Reference, $51^{st}$ Edition, p. 2805.

A.P.L.®, Physicians' Desk Reference, $12^{th}$ Edition, p. 625.

A.P.L.®, Physicians' Desk Reference, $19^{th}$ Edition, p. 537.

A.P.L.®, Physicians' Desk Reference, $34^{th}$ Edition, p. 592.

Arzneiformenlehre, Paul Heinz List, Wissenschaftliche Verlagsgellschaft mbH, Stuttgart, 4th Edition, 1985, pp. 402-407.

Asellacrin®, Physicians' Desk Reference, $34^{th}$ Edition, pp. 1605-1606.

Asellacrin®, Physicians' Desk Reference, $39^{th}$ Edition, pp. 1940-1941.

Boime, Irving et al., "Glycoprotein Hormone Structure-Function and Analog Design", Recent Progress in Hormone Research, vol. 54, 1999, The Endocrine Society, pp. 271-289.

Bontempo, John A., "Chapter 5: Formulation Development", Development of Biopharmaceutical Parenteral Dosage Forms, pp. 109-142, published by Marcel Dekker, Inc.

Combarnous, Yves, "Molecular Basis of the Specificity of Binding of Glycoprotein Hormones to Their Receptors", Endocrine Reviews, 1992. vol. 13, No. 4, pp. 670-691.

CPMP Guidelines antimicrobial preservative inclusion, CPMP/CVMP/OWP/115/95, Jul. 8, 1997, pp. 1-6.

de Medeiros, S.F. et al., "Stability of Immunoreative β-Core Fragment of hCG", Obstetrics & Gynecology, vol. 77, No. 1, Jan. 1991, pp. 53-59.

Epogen®, Physicians' Desk Reference, $51^{st}$ Edition, pp. 489-494.

Fertinex™ (urofollitropin for injection, purified) for subcutaneous injection, Physicians' Desk Reference, $53^{rd}$ Edition, pp. 2988-2989, published by Medical Economics Company, Inc.

Fertinex®, Physicians' Desk Reference, $55^{th}$ Edition, pp. 3020-3022.

Follistim™ (follitropin beta for injection), Physicians' Desk Reference, $53^{rd}$ Edition, pp. 2128-2132, published by Medical Economics Company, Inc.

Follistim®, Physicians' Desk Reference, $54^{th}$ Edition, pp. 2092-2095.

Follutein®, Physicians' Desk Reference, $24^{th}$ Edition, pp. 1249-1250.

Fransson, Jonas et al., "Solvent Effects on the Solubility and Physical Stability of Human Insulin-Like Growth Factor 1", Pharmaceutical Research 14(5):606-12, 1997.

Frenken, L.A.M. et al., "Analysis of the Efficacy of Measures to Reduce Pain After Subcutaneous Administration of Epoetin Alfa", Nephrology Dialysis Transplantation 9:1295-98, 1994.

Furuhashi, M. et al. "Fusing the Carboxy-Terminal Peptide of the Chorionic Gonadotropin (CG) beta Subunit to the Common alpha- Subunit: Retention of O-linked Glycosylation and Enhanced in Vivo Bioactivity of Chimeric Human CG", Molecular Endocrinology, 1995, vol. 9, No. 1, pp. 54-63.
Garcia-Campayo, Vincenta et al., "Design of Stable Biologically Active Recombinant Lutropin Analogs", Nature Biotechnology 15:663-67, 1997.
Gennaro et al., "Parenteral Preparations", Chapter 84, Remington's Pharmaceutical Sciences (18th Edition, Mack Publishing. Co., 1990, see part 8 "Pharmaceutical Preparations and their Manufacture," pp. 1545-1569.
Glucagon, Physicians' Desk Reference, 19$^{th}$ Edition, pp. 703-704.
Glukor®, Physicians' Desk Reference, 19$^{th}$ Edition, p. 844.
Gonal-F®, (follitropin alfa for injection), for subcutaneous injection, Physicians' Desk Reference, 53$^{rd}$ Edition, pp. 2991-2995, published by Medical Economics Company, Inc.
Gonal-F® (follitropin alfa for injection) for subcutaneous injection: Package Insert Code N1900101B, manufactured by Serono Laboratories, Inc., Randolph, MA, USA, published Sep. 1997.
Gonal-F®, Physicians' Desk Reference, 54$^{th}$ Edition, pp. 2942-2946.
Hanson, Musetta A. et al., "Introduction to Formulation of Protein Pharmaceuticals", Chapter. 7, pp. 209-233.
Harvey, Stewart C., "Antiseptics and Disinfectants; Fungicides; Ectoparasiticides", The Pharmacological Basis of Therapeutics, 6$^{th}$ Edition, Chapter 41, 964-987, 1980.
Heikoop, Judith C. et al., "Structure-based design and protein engineering of intersubunit disulfide bonds in gonadotropins" Nature Biotechnology, Jul. 1997, vol. 15, pp. 658-662.
Package insert HRF, "HRF Injection 0,1 mg and HRF Injection 0,5 mg", Malahyde Information Systems, 2003, pp. 1-4.
Humatrope®, Physicians' Desk Reference, 44$^{th}$ Edition, pp. 1216-1217.
Humegon®, Physicians' Desk Reference, 54$^{th}$ Edition, pp. 2095-2097.
Jorgenson, Jan Trost, "Improvement of Patient Convenience in Treatment with Growth Hormone", Journal of Pediatric Endocrinology, 1994, 7(2):175-180.
Keene et al., Expression of Biologically Active Human Follitropin in Chinese Hamster Ovary Cells. The Journal of Biological Chemistry vol. 264/9: 4769-4775.
Kesner, J.S. et al., "Stability of Urinary Female Reproductive Hormones Stored Under Various Conditions", Reproductive Toxicology, vol. 9, No. 3, pp. 239-244, 1995.
Lam, Xanthe M. et al., "The Effect of Benzyl Alcohol on Recombinant Human Interferon-γ" Pharmaceutical Research, 1997, vol. 14, No. 6, 725-729.
Leukine Package Insert/Approved Text, Rev. 0230-02, Issued Feb. 1998, pp. 1-30.
Livesey J. H. et al., "Glycerol prevents loss of immunoreactive follicle-stimulating hormone and luteinizing hormone from frozen urine", Journal of Endocrinology, vol. 98, pp. 381-384, 1983.
Livesey, J. H. et al., "Effect of Time, Temperature and Freezing on the Stability of Immunoreative LH, FSH, TSH, Growth Hormone, Prolactin and Insulin in Plasma", The Medical Unit, Princess Margaret Hospital, Christchurch 2, New Zealand, Jun. 25, 1980, Biochem 13(4), 1980, pp. 151-155.
Maa, Yuh-Fun, et al., "Aggregation of recombinant human growth hormone induced by phenolic compounds", International Journal of Pharmaceutics, 1996, vol. 140, pp. 155-168.
Metrodin®, Physicians' Desk Reference, 51$^{st}$ Edition, pp. 2616-2618.
Pergonal®, Physician's Desk Reference, 29$^{th}$ Edition, pp. 1366-1367.
Pergonal®, Physician's Desk Reference, 49$^{th}$ Edition, pp. 2335-2337.
Pergonal®, Physician's Desk Reference, 51$^{st}$ Edition, pp. 2618-2620.
Pergonal®, Physician's Desk Reference, 54$^{th}$ Edition, pp. 2946-2947.
Pimpalkhute, M. et al., "Radioimmunoassay of Human Follicle Stimulating Hormone/HFSH/", J. Radioanal. Nucl. Chem. Letters, 1986, 103, No. 2, pp. 105-116.
Pregnyl®, Physicians' Desk Reference, 39$^{th}$ Edition, p. 1450.
Pregnyl® (chorionic gonadotropin for injection, USP), Physicians' Desk Reference, 51$^{st}$ Edition, p. 1878.
Pregnyl Prescribing Information, Pregnyl (chorionic gonadotropin for injection, USP), Organon Inc., Aug. 1998, pp. 1-4.
Procrit®, Physicians' Desk Reference, 51$^{st}$ Edition, p. 1896.
Profasi® (chorionic gonadotropin for injection, USP) for Intramuscular Injection, Physicians' Desk Reference, 51$^{st}$ Edition, pp. 2620-2621.
Profasi (chorionic gonadotropin for injection, USP) for intramuscular injection, Serono Laboratories, Inc. (revised Jun. 1993).
Progon®, Physicians' Desk Reference, 19$^{th}$ Edition, p. 646.
Protropin®, Physicians' Desk Reference, 44$^{th}$ Edition, pp. 1002-1003.
Rafferty, M.J. et al., "Safety and Tolerability of a Multidose Formulation of Epoetin Beta in Dialysis Patients", Clinical Nephrology. 54(3):240-45, 2000.
Regular Iletin®, Physicians' Desk Reference 19$^{th}$ Edition, p. 705.
Remmele Jr., Richard L. et al., "Interleukin-1 Receptor (IL-1R) Liquid Formulation Development Using Differential Scanning Calorimetry", Pharmaceutical Research, 1998, vol. 15, No. 2 pp. 200-208.
Rose, M.P. et al, "Characterisation, calibration and comparison by international collaborative study of international standards for the calibration of therapeutic preparations of FSH", Journal of Endocrinology, vol. 158, pp. 97-114, 1998.
Ryan, Robert J. et al., "Some physical and Hydrodynamic Properties of Human FSH and LH", Mayo Clinic and Mayo Foundation: Section of Endocrine Research, Rochester, Minnesota; and Department of Biochemistry, University of Illinois, Chicago, Illinois, pp. 105-137.
St. Peter, Wendy L. et al., "Pain Comparison After Subcutaneous Administration of Single-Dose Formulation Versus Multidose Formulation of Epogen in Hemodialysis Patients", American Journal of Kidney Diseases, 32(3):470-74, 1998.
Saizen®, Physicians' Desk Reference, 52$^{nd}$ Edition, pp. 2776-2777.
Saketos, Maria et al., "Time-Resolved Immunofluorometric Assay and Specimen Storage Conditions for Measuring Urinary Gonadotropins", Clinical Chemistry, vol. 40, No. 5, 1974, pp. 749-753.
Saxena, B.B. et al., "Amino Acid Sequence of the β Subunit of Follicle-stimulating Hormone from Human Pituitary Glands", The Journal of Biological Chemistry, vol. 251, No. 4, pp. 993-1005, Feb. 25, 1976.
Serono Study Report GF 9873, "Evaluation of FSH Formulations claimed in EP-974'359", dated Mar. 22, 2004.
Shoemaker, J. et al., "New Approaches with the FSH Threshold Principle in Polycystic Ovarian Syndrome", Annals New York Academy of Sciences, pp. 296-300.
Shome, B. et al., "Human Follicle Stimulating Hormone: First Proposal for the Amino Acid Sequence of the Hormone-Specific, β Subunit (hFSHβ)", J. Clin. Endocrinol. Metab., vol. 39, 187, pp. 203-205, 1974.
Stemutrolin®, Physicians' Desk Reference, 24$^{th}$ Edition, p. 867.
Strickland, Thomas W. et al, "The Kinetic and Equilibrium Parameters of Subunit Association and Gonadotropin Dissociation", The Journal of Biological Chemistry, 1982, vol. 257, No. 6 pp. 2954-2960.
Package insert Suprefact.
Sugahara, Tadashi et al., "Expression of biologically active fusion genes encoding the common α subunit and either the CGβ or FSHβ subunits: role of a linker sequence", Molecular and Cellular Endocrinology 125 (1996) pp. 71-77.
"The United States Pharmacopeia, Twenty-First Revision", United States Pharmacopeial Convention, Inc., Official from Jan. 1, 1985, prepared by the Committee of Revision and published by the Board of Trustees, pp. 1491-1493, 1984.
Vahl, et al., "Bioavailability of Recombinant Human Growth Hormone in Different Concentrations and Formulations", Pharmacology & Toxicology 79:144-49, 1996.
Voortman, Gerritt et al, "Bioequivalence of subcutaneous injections of recombinant human follicle stimulating hormone (Puregon®) by Pen-injector and syringe", Human Reproduction, 1999, vol. 14, No. 7, pp. 1698-1702.

Wallhausser K-H, "Antimicrobial Preservatives in Europe: Experience with Preservatives Used in Pharmaceuticals and Cosmetics", International Symposium on Preservation in Biological Products, San Francisco 1973, Develop. Biol. Standard, vol. 24, pp. 9-28, 1974.

Anchordoquy, Thomas J. et al., "Polymers Protect Lactate Dehydrogenase during Freeze-Drying by Inhibiting Dissociation in the Frozen State", Archives of Biochemistry and Biophysics, vol. 332, No. 2, Aug. 15, 1996, Article No. 0337, pp. 231-238.

Anik, Shabbir T. et al., "Adsorption of D-Nal(2) $^6$LHRH, a decapeptide, onto glass and other surfaces", Institute of Pharmaceutical Sciences, Syntax Research, Palo Alto, CA, International Journal of Pharmaceutics, vol. 16, 1983, pp. 181-190.

Bam, Narendra B. et al. "Stability of Protein Formulations: Investigation of Surfactant Effects by a Novel EPR Spectroscopic Technique", Research Article, Pharmaceutical Research, vol. 12, No. 1, 1995, pp. 2-11.

Baselga, Jose et al., "Phase II Study of Weekly Intravenous Recombinant Humanized Anti-p185$^{HER2}$ Monoclonal Antibody in Patients with HER2/neu-Overexpressing Metastic Breast Cancer", Journal of Clinical Oncology, vol. 14, No. 3, Mar. 1996, pp. 737-744.

Boulet, Louis-Philippe et al., "Inhibitory Effects of an Anti-IgE Antibody E25 on Allergen-induced Early Asthmatic Response", Am J Respir Crit Care Med., vol. 155, 1997, pp. 1835-1840.

Butt, W. R., "The Iodination of Follicle-Stimulating and Other Hormones for Radioimmunossay", J. Endocr., 1972, vol. 55, pp. 453-454.

Jentoft, Neil, "Why are proteins O-glycosylated?", TIBS 15, Aug. 1990, Elsevier Sciences Publishers Ltd. (UK), pp. 291-294.

Ketelslegers, J.-M et al., "Receptor Binding Properties of $^{125}$I-hFSH Prepared by Enzymatic Iodinzation", Submitted Aug. 30, 1974, J. Clin. Endocrinol Metabl, vol. 39, No. 6, 1974, pp. 1159-1162.

Kibbe, Arthur H. (Editor), "Benzyl Alcohol", Handbook of Pharmaceutical Excipients, Third Edition, American Pharmaceutical Association, 2000, pp. 41-43.

Marana, R. et al., "Influence of the Purity of the Iodinated Tracer on the Specificity of the Radioimmunoassay of Human Follicle-Stimulating Hormone", Acta Endocrinologica, vol. 92, 1979, pp. 585-598.

Miyachi, Yukitaka, et al., "Structural Integrity of Gonadotropins after Enzymatic Iodination", Biochemical and Biophysical Research Communications, vol. 46, No. 3, 1972, pp. 1213-1221.

Mizutani, Takaharu et al., "Estimation of Adsorption of Drugs and Proteins on Glass Surfaces with Controlled Pore Glass as a Reference", Journal of Pharmaceutical Sciences, vol. 67., No. 8, Aug. 1978, American Pharmaceutical Association, pp. 1102-1105.

Mizutani, Takaharu, et al., "Study of Protein Adsorption on Glass Surfaces with a Hydrophobic Fluorescent Probe", Chem. Pharm. Bulletin, vol. 32, No. 6, 1984, pp. 2395-2400.

Pikal, Michael J. et al., "The Effects of Formulation Variables on the Stability of Freeze-Dried Human Growth Hormone", Pharmaceutical Research, vol. 8, No. 4, 1991, pp. 427-436.

Pinto, Heidi et al., "Preparation of High-Quality Iodine-125-Labelled Pituitary Human Follicle-Stimulating Hormone (hFSH) for Radioimmunoassay: Comparison of Enzymatic and Chloramine-T Iodination", Clinica Chimica Acta, Elsevier/North-Holland Biomedical Press, vol. 76, 1977, pp. 25-34.

Rathnam, P. et al., "Studies on Modification of Tryptophan, Methionine, Tyrosine and Arginine Residues of Human Follicle-Stimulating Hormone and Its Subunits", Biochimica et Biophysica Acta, vol. 576, 1979, Elsevier/North-Holland Biomedical Press, pp. 81-87.

Silberring, Jerzy et al., "A Universal and Simple Chloramine T Version for Hormone Iodination", International Journal of Applied Radiation and Isotopes, vol. 33, 1982, pp. 117-119.

Stankov, B. M. et al., "The Effect of the Purity of the Iodinated Tracer on the Specificity of a Homologous Assay of Ovine Follicle Stimulating Hormone", Biochemistry International, vol. 12, No. 1, Jan. 1986, pp. 11-19.

Suginami, H. et al., "Influence of the Purity of the Iodinated Tracer on the Specificity of the Radioimmunoassay of Human Luteinizing Hormone", Acta Endocrinologica, vol. 89, 1978, pp. 506-520.

Swinyard, Ewart et al., "Pharmaceutical Necessities", Chapter 68, pp. 1278-1280.

Terada, Shigeyuki, "Iodination of Luteinizing Hormone-Releasing Hormone", Biochemistry 1980, vol. 19, pp. 2572-2576.

"Urofollitropin", European Pharmacopia 2001, 1997:0958 (last revised version of 2001), pp. 1-6.

Van den Steen, Philippe et al., "Concepts and Principles of O-Linked Glycosylation", hCG papers / CTP extensions / Boime papers, Critical Reviews in Biochemistry and Molecular Biology, vol. 35, No. 3, 1998, pp. 151-208.

Wang, Yu-Chang John et al., "Review of Excipients and pH's for Parenteral Products Used in the United States", Journal of the Parenteral Drug Association, vol. 34, No. 6, Nov.-Dec. 1980, pp. 452-462.

Walsh, Gary, "Pharmaceutical biotechnology products approved within the European Union", European Journal of Pharmaceutics and Biopharmaceutics, vol. 55, 2003, pp. 3-10.

Waterman, Kenneth C. et al., "Stabilization of Pharmaceuticals to Oxidative Degradation", Pharmaceutical Development and Technology, vol. 7, No. 1, 2002, pp. 1-32.

Xing, Yongna et al., "Threading of a glycosylated protein loop through a protein hole: Implications for combination of human chorionic gonadotropin subunits", Protein Science, vol. 10, 2001, pp. 226-235.

Katakam et al., Effect of surfactants on the physical stabilit of recombinant human growth hormone; Jornal of Pharmaceutical Sciences Jun. 1995; 84(6): 713-716.

Katakam et al., Use of poloxamer polymers to stabilize recombinant human growth hormone against various processing stress; Pharm. Dev. Technol. May 1997; 2(2):143-9.

Lee, Peptide and protein drug delivery, 1991.

Swarbick et al, Encyclopedia of pharmaceutical technology, vol. 19, 2000, p. 1643.

* cited by examiner

SEQUENCE LISTING

<160> NUMBER OF SEQ ID NOS: 6

<210> SEQ ID NO 1
<211> LENGTH: 91
<212> TYPE: PRT
<213> ORGANISM: Homo sapiens

<400> SEQUENCE: 1

```
Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
                20                  25                  30

Phe Ser Arg Ala Tyr Pro Thr Pro Leu Arg Ser Lys Lys Thr Met Leu
            35                  40                  45

Val Gln Lys Asn Val Thr Ser Glu Ser Thr Cys Cys Val Ala Lys Ser
        50                  55                  60

Tyr Asn Arg Val Thr Val Met Gly Gly Phe Val Glu Asn His Thr Ala
65                  70                  75                  80

Cys His Cys Ser Thr Cys Tyr Tyr His Lys Ser
                85                  90
```

<210> SEQ ID NO 2
<211> LENGTH: 129
<212> TYPE: PRT
<213> ORGANISM: Homo sapiens

<400> SEQUENCE: 2

```
Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
        50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125
```

-continued

Glu

<210> SEQ ID NO 3
<211> LENGTH: 108
<212> TYPE: PRT
<213> ORGANISM: Homo sapiens

<400> SEQUENCE: 3

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu
            100                 105

<210> SEQ ID NO 4
<211> LENGTH: 106
<212> TYPE: PRT
<213> ORGANISM: Homo sapiens

<400> SEQUENCE: 4

Asn Ser Cys Glu Leu Thr Asn Ile Ala Ile Glu Lys Glu Cys Arg
1               5                   10                  15

Phe Cys Ile Ser Ile Asn Thr Trp Cys Ala Gly Tyr Cys Tyr Thr Arg
            20                  25                  30

Asp Leu Val Tyr Lys Asp Pro Ala Arg Pro Lys Ile Gln Lys Thr Cys
        35                  40                  45

Thr Phe Lys Glu Leu Val Tyr Glu Thr Val Arg Val Pro Gly Cys Ala
    50                  55                  60

His His Ala Asp Ser Leu Tyr Thr Val Pro Val Ala Thr Gln Cys His
65                  70                  75                  80

Cys Gly Lys Cys Asp Ser Asp Ser Thr Asp Cys Thr Val Arg Gly Leu
                85                  90                  95

Gly Pro Ser Tyr Cys Ser Phe Gly Glu Met
            100                 105

<210> SEQ ID NO 5
<211> LENGTH: 110
<212> TYPE: PRT
<213> ORGANISM: Homo sapiens

<400> SEQUENCE: 5

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

-continued

```
Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys
                100                 105                 110

<210> SEQ ID NO 6
<211> LENGTH: 112
<212> TYPE: PRT
<213> ORGANISM: Homo sapiens

<400> SEQUENCE: 6

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Arg Val Leu Gln Ala Val Leu
            35                  40                  45

Pro Pro Leu Pro Gln Val Cys Thr Tyr Arg Asp Val Arg Phe Glu Ser
        50                  55                  60

Ile Arg Leu Pro Gly Cys Pro Arg Gly Val Asp Pro Val Val Ser Phe
65                  70                  75                  80

Pro Val Ala Leu Ser Cys Arg Cys Gly Pro Cys Arg Arg Ser Thr Ser
                85                  90                  95

Asp Cys Gly Gly Pro Lys Asp His Pro Leu Thr Cys Asp His Pro Gln
                100                 105                 110
```

LIQUID PHARMACEUTICAL FORMULATIONS OF FSH AND LH TOGETHER WITH A NON-IONIC SURFACTANT

FIELD OF INVENTION

The invention relates to the field of pharmaceutical formulations of follicle-stimulating hormone (FSH), formulations of luteinising hormone (LH), and mixtures of FSH and luteinising hormone (LH); as well as to methods of producing such formulations.

BACKGROUND OF THE INVENTION

Follicle-stimulating hormone (FSH) luteinising hormone (LH) and chorionic gonadotrophin (CG) are injectable proteins falling into the class of gonadotrophins. FSH, LH and hCG are used alone and in combination in the treatment of infertility and reproductive disorders in both female and male patients.

In nature, FSH and LH are produced by the pituitary gland. For pharmaceutical use, FSH and LH and their variants may be produced recombinantly (rFSH and rLH), or they may be produced from the urine of postmenopausal women (uFSH and uLH).

FSH is used in female patients in ovulation induction (OI) and in controlled ovarian hyperstimulation (COH) for assisted reproductive technologies (ART). In a typical treatment regimen for ovulation induction, a patient is administered daily injections of FSH or a variant (about 75 to 300 IU FSH/day) for a period of from about 6 to about 12 days. In a typical treatment regimen for controlled ovarian hyperstimulation, a patient is administered daily injections of FSH or a variant (about 150-600 IU FSH/day) for a period of from about 6 to about 12 days.

FSH is also used to induce spermatogenesis in men suffering from oligospermia. A regimen using 150 IU FSH 3 times weekly in combination with 2,500 IU hCG twice weekly has been successful in achieving an improvement in sperm count in men suffering from hypogonadotrophic hypogonadism[1].

LH is used in female patients in combination with FSH in OI and in COH, particularly in those patients having very low endogenous LH levels or resistance to LH, such as women suffering from hypogonadotrophic hypogonadism (HH, WHO group I) or older patients (i.e. 35 years or older), and patients in which embryo implantation or early miscarriage is a problem. LH in combination with FSH has traditionally been available in a preparation called human menopausal gonadotrophins (hMG) extracted from the urine of postmenopausal women. hMG has a 1:1 ratio of FSH:LH activity.

CG acts at the same receptor as LH and elicits the same responses. CG has a longer circulation half-life than LH and is therefore commonly used as a long-acting source of LH-activity. CG is used in OI and COH regimens to mimic the natural LH peak and trigger ovulation. An injection of human chorionic gonadotrophin (hCG) is used to trigger ovulation at the end of stimulation with FSH or a mixture of FSH and LH. CG may also be used together with FSH during stimulation for OI and COH, in order to provide LH-activity during stimulation in patients in which LH-activity is desirable, such as those mentioned above.

FSH, LH and CG are members of the heterodimer, glycoprotein hormone family that also includes thyroid stimulating hormone (TSH). The members of this family are heterodimers, comprising an α- and a β-subunit. The subunits are held together by noncovalent interactions. The human FSH (hFSH) heterodimer consists of (I) a mature 92 amino acid glycoprotein alpha subunit, which also is common to the other human family members (i.e., chorionic gonadotrophin ("CG"), luteinising hormone ("LH") and thyroid stimulating hormone ("TSH"); and (ii) a mature 111 amino add beta subunit that is unique to FSH[2]. The human LH heterodimer consists of (i) the mature 92 amino acid glycoprotein alpha subunit; and (ii) a mature 112 beta subunit that is unique to LH[3]. The alpha and beta subunits of the glycoproteins may be prone to dissociate in formulations, due to interaction with a preservative, surfactant and other excipients. Dissociation of the subunits leads to loss of biological potency[4].

FSH is formulated for intramuscular (IM) or subcutaneous (SC) injection. FSH is supplied in lyophilised (solid) form in vials or ampoules of 75 IU/vial and 150 IU/vial with a shelf life of one and a halt to two years when stored at 2-25° C. A solution for injection is formed by reconstituting the lyophilised product with water for injection (WFI). For ovulation induction or controlled ovarian hyperstimulation, daily injections with starting doses of 75 IU to 600 IU are recommended for up to about ten days. Depending on the patients response, up to three cycles of treatment with increasing doses of FSH can be used. With lyophilised formulations, the patient is required to reconstitute a new vial of lyophilised material with diluent and administer it immediately after reconstitution on a daily basis [Package insert N1700101A, published in February 1996, for Fertinex™ (urofollitropin for injection, purified) for subcutaneous injection, by Serono Laboratories, Inc., Randolph, Mass.].

FSH has also been formulated in both single-dose and multi-dose liquid formats, in vials, or ampoules. Single dose formats must remain stable and potent in storage prior to use. Multi-dose formats must not only remain stable and potent in storage prior to use, but must also remain stable, potent and relatively free of bacteria over the multiple-dose use regimen administration period, after the seal of the ampoule has been compromised. For this reason, multi-dose formats often contain a bacteriostatic agent.

LH is formulated for intramuscular (IM) or subcutaneous (SC) injection. LH is supplied in lyophilised (solid) form in vials or ampoules of 75 IU/vial with a shelf life of one and a half to two years when stored at 2-25° C. A solution for injection is formed by reconstituting the lyophilised product with water for injection (WFI). For ovulation induction or controlled ovarian hyperstimulation, in conjunction with FSH, daily injections with starting doses of 75 IU to 600 IU LH are recommended for up to about ten days.

EP 0 618 808 (Applied Research Systems ARS Holding N.V.) discloses a pharmaceutical composition comprising a solid intimate mixture of gonadotrophin and a stabilising amount of sucrose alone or in combination with glycine.

EP 0 814 841 (Applied Research Systems ARS Holding N.V.) discloses a stable, liquid pharmaceutical composition comprising recombinant human chorionic gonadotrophin (hCG) and a stabilizing amount of mannitol.

EP 0 448 146 (AKZO N.V.) discloses a stabilized gonadotrophin containing lyophilisate comprising one part by weight of a gonadotrophin; and 200 to 10,000 parts by weight of a dicarboxylic acid salt stabilizer associated with the gonadotrophin.

EP 0 853 945 (Akzo Nobel N. V.) discloses a liquid gonadotrophin-containing formulation characterised in that the formulation comprises a gonadotrophin and stabilising amounts of a polycarboxylic acid or a salt thereof and of a thioether compound.

WO 00/04913 (Eli Lilly and Co.) discloses a formulation comprising FSH or an FSH variant, containing an alpha and beta subunit and a preservative selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof in an aqueous diluent.

There remains a need for stable liquid formulations of FSH or FSH variants, and mixtures of FSH and LH, either for single dose or multiple dose administration.

SUMMARY OF THE INVENTION

It is an object of the invention to provide new freeze dried as well as liquid formulations of FSH or FSH variants, LH or LH variants, to provide methods for their preparation, and methods for their pharmaceutical or veterinary use in the treatment of fertility disorders.

It is a further object of the invention to provide new freeze dried and liquid formulations of mixtures of FSH and LH, to provide methods for their preparation, and methods for their pharmaceutical or veterinary use in the treatment of fertility disorders.

In a first aspect, the invention provides a freeze dried and liquid pharmaceutical composition comprising FSH or a variant thereof, and a surfactant selected from block copolymers of ethylene oxide and propylene oxide, preferably Pluronic® F77, Pluronic F87, Pluronic F88 and Pluronic F68.

In a second aspect, the invention provides a method for manufacturing a liquid pharmaceutical composition comprising forming a solution of FSH or a variant thereof, and a surfactant selected from block copolymers of ethylene oxide and propylene oxide, preferably Pluronic® F77, Pluronic F87, Pluronic F88 and Pluronic F68 and WFI.

In a third aspect, the invention provides a method for manufacturing a packaged pharmaceutical composition comprising dispensing a solution comprising FSH, and a surfactant selected from block copolymers of ethylene oxide and propylene oxide, preferably Pluronic® F77, Pluronic F87, Pluronic F88 and Pluronic F68, into a container.

In a fourth aspect, the invention provides an article of manufacture for human pharmaceutical use, comprising a vial comprising a solution of FSH or an FSH variant, and a surfactant selected from block copolymers of ethylene oxide and propylene oxide, preferably Pluronic® F77, Pluronic F87, Pluronic F88 and Pluronic F68 and written material stating that such solution may be held over a period of at or about twenty-four hours or greater after the first use.

In a fifth aspect, the invention provides a freeze dried and liquid pharmaceutical composition comprising FSH and LH, and a surfactant selected from block copolymers of ethylene oxide and propylene oxide preferably Pluronic® F77, Pluronic F87, Pluronic F88 and Pluronic F68.

In a sixth aspect the invention provides a method for manufacturing a freeze dried and liquid pharmaceutical composition comprising forming a solution of FSH and LH and a surfactant selected from selected from block copolymers of ethylene oxide and propylene oxide, preferably Pluronic® F77, Pluronic F87, Pluronic F88 and Pluronic F68.

In an seventh aspect, the invention provides a method for manufacturing a packaged pharmaceutical composition comprising dispensing a solution comprising FSH and LH, and a surfactant selected from block copolymers of ethylene oxide and propylene oxide, preferably Pluronic® F77, Pluronic F87, Pluronic F88 and Pluronic F68, into a container.

In an eighth aspect, the invention provides an article of manufacture for human pharmaceutical use, comprising a vial comprising a solution of FSH and LH, and a surfactant selected from block copolymers of ethylene oxide and propylene oxide, preferably Pluronic® F77, Pluronic F87, Pluronic F88 and Pluronic F68 and written material stating that such solution may be held over a period of at or about twenty-four hours or greater after the first use.

In a ninth aspect the invention provides an article of manufacture for human pharmaceutical use, comprising a first container comprising freeze dried FSH or an FSH variant and a surfactant selected from block copolymers of ethylene oxide and propylene oxide, preferably Pluronic® F77, Pluronic F87, Pluronic F88 and Pluronic F68 and a second container comprising a solvent for reconstitution, preferably an aqueous solution containing a bacteriostatic, preferably m-cresol.

In an tenth aspect, the invention provides an article of manufacture for human pharmaceutical use, comprising a first container comprising freeze dried LH or an LH variant, and a surfactant selected from block copolymers of ethylene oxide and propylene oxide, preferably Pluronic® F77, Pluronic F87, Pluronic F88 and Pluronic F68 and a second container comprising a solvent for reconstitution, preferably an aqueous solution containing a bacteriostatic, preferably m-cresol.

In an eleventh aspect, the invention provides an article of manufacture for human pharmaceutical use, comprising a first container comprising freeze dried FSH as well as LH or an FSH or LH variant, and a surfactant selected from block copolymers of ethylene oxide and propylene oxide, preferably Pluronic® F77, Pluronic F87, Pluronic F88 and Pluronic F68 and a second container comprising a solvent for reconstitution, preferably an aqueous solution with m-cresol.

DETAILED DESCRIPTION OF THE INVENTION

Figure 1:
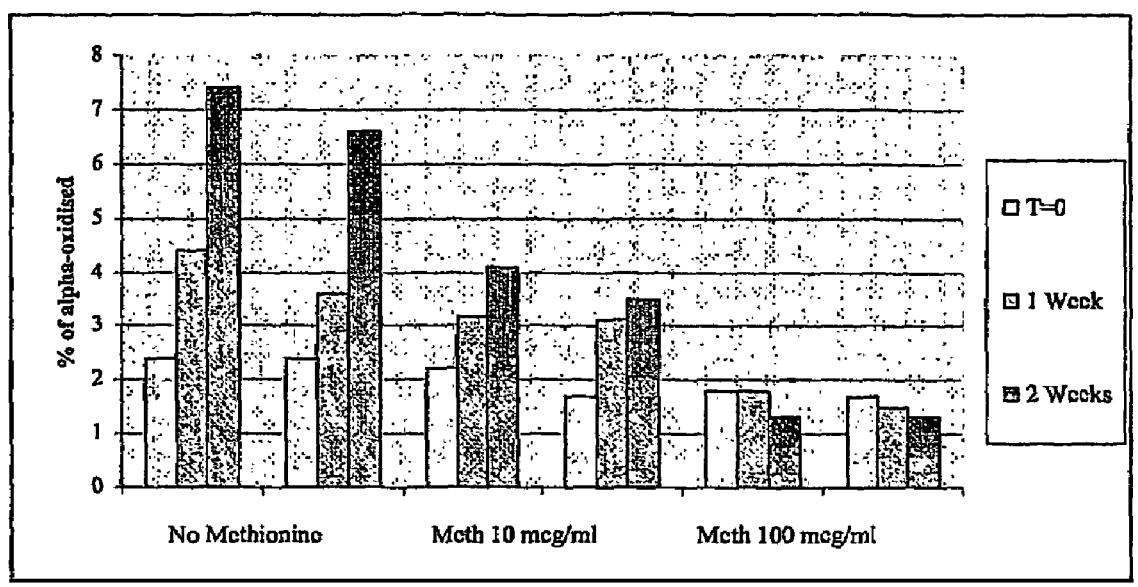
FIG. 1 shows the percentage of oxidised α-subunit in formulations of FSH containing Pluronic F68, methionine at 10 μg/ml ("Meth 10 mcg/ml") and 100 μg/ml ("Meth 100 mcg/ml") versus a formulation with no methionine ("No methionine"), at time 0, 1 week and 2 weeks.

The liquid and freeze dried FSH or FSH and LH formulations of the invention have improved or more suitable properties or stability, and are useful for infertility treatment in women and/or men. These formulations and articles of manufacture are additionally suitable for use in injectable and alternative delivery systems, e.g., but not limited to, nasal, pulmonary, transmucosal, transdermal, oral, subcutaneous, intramuscular or parenteral sustained release. In a particularly preferred embodiment the formulations of the invention are for subcutaneous and/or intramuscular injection. The FSH or FSH and LH variant solutions and formulations provided may also have increased in vivo potency over time compared to known commercial products, by preventing or reducing loss of activity or stability, or by improving any aspect of the effectiveness or desirability of administration, e.g., by at least one of mode, frequency, dosage, comfort, ease of use, biological activity in vitro or in vivo, and the like.

Follicle stimulating hormone, or FSH, as used herein refers to the FSH produced as a full-length mature protein which includes, but is not limited to human FSH or "hFSH", whether produced recombinantly or isolated from human sources, such as the urine of postmenopausal women. The protein sequence of the human glycoprotein alpha subunit is provided in SEQ ID NO: 1, and the protein sequence of the human FSH beta subunit is given in SEQ ID NO:2.

The expression "FSH variant" is meant to encompass those molecules differing in amino acid sequence, glycosylation pattern or in inter-subunit linkage from human FSH but exhibiting FSH-activity. Examples include CTP-FSH, a long-acting modified recombinant FSH, consisting of the wild type α-subunit and a hybrid β-subunit in which the carboxy terminal peptide of hCG has been fused to the C-terminal of the β-subunit of FSH, as described in LaPolt et al.; Endocrinology; 1992, 131, 2514-2520; or Klein et al.; Development and characterization of a long-acting recombinant hFSH agonist Human Reprod. 2003, 18, 50-56]. Also included is single chain CTP-FSH, a single chain molecule, consisting of the following sequences (from N-terminal to C-terminal):

| βFSH | βhCG-CTP(113-145) | αFSH |
| --- | --- | --- | wherein βFSH signifies the β-subunit of FSH, βhCG CTP (113-145) signifies the carboxy terminal peptide of hCG and αFSH signifies the α-subunit of FSH, as described by Klein et al.[5] Other examples of FSH variants include FSH molecules having additional glycosylation sites incorporated in the α- and/or βsubunit as disclosed in WO 01/58493 (Maxygen), particularly as disclosed in claims 10 and 11 of WO 01/58493, and FSH molecules with intersubunit S—S bonds, as disclosed in WO 98/58957.

The FSH variants referred to herein also include the carboxy terminal deletions of the beta subunit that are shorter than the fun length mature protein of SEQ ID NO:2. Carboxy terminal deletions of the human beta subunit are provided in SEQ IDS NOS: 3, 4, and 5. It is understood that the carboxy terminal variants of the beta chain form dimers with a known alpha subunit to form an FSH variant heterodimer.

FSH heterodimers or FSH variant heterodimers can be produced by any suitable method, such as recombinantly, by isolation or purification from natural sources as may be the case, or by chemical synthesis, or any combination thereof.

The use of the term "recombinant" refers to preparations of FSH, LH or FSH and LH variants that are produced through the use of recombinant DNA technology (see for example WO 85/01958). The sequences for genomic and cDNA clones of FSH are known for the alpha and beta subunits of several species[6]. One example of a method of expressing FSH or LH using recombinant technology is by transfection of eukaryotic cells with the DNA sequences encoding an alpha and beta subunit of FSH or LH, whether provided on one vector or on two vectors with each subunit having a separate promoter, as described in European patent nos. EP 0 211 894 and EP 0 487 512 Another example of the use of recombinant technology to produce FSH or LH is by the use of homologous recombination to insert a heterologous regulatory segment in operative connection to endogenous sequences encoding the subunits of FSH or LH, as described in European patent no. EP 0 505 500 (Applied Research Systems ARS Holding NV).

The FSH or FSH variant used in accordance with the present invention may be produced not only by recombinant means, including from mammalian cells, but also may be purified from other biological sources, such as from urinary sources. Acceptable methodologies include those described in Hakola, K. Molecular and Cellular Endocrinology, 127:59-69, 1997; Keene, et al., J. Biol. Chem., 264:4769-4775, 1989; Cerpa-Poljak et al., Endocrinology, 132:351-356, 1993; Dias, et al., J. Biol. Chem., 269:25289-25294, 1994; Flack, et al., J. Biol. Chem., 269:14015-14020, 1994; and Valove, et al., Endocrinology, 135:2657-2661, 1994, U.S. Pat. No. 3,119,740 and U.S. Pat. No. 5,767,067.

Luteinising hormone, or LH, as used herein refers to the LH produced as a full length mature protein, which includes, but is not limited to human LH or "hLH", whether produced recombinantly or isolated from human sources, such as the urine of postmenopausal women. The protein sequence of the human glycoprotein alpha subunit is provided in SEQ ID NO: 1, and the protein sequence of the human LH beta subunit[7] is given in SEQ ID NO: 6. In a preferred embodiment the LH is recombinant.

The expression "LH variant" is meant to encompass those molecules differing in amino acid sequence, glycosylation pattern or in inter-subunit linkage from human LH but exhibiting LH-activity.

LH heterodimers or LH variant heterodimers can be produced by any suitable method, such as recombinantly, by isolation or purification from natural sources as may be the case, or by chemical synthesis, or any combination thereof.

The term "administer" or "administering" means to introduce a formulation of the present invention into the body of a patient in need thereof to treat a disease or condition.

The term "patient" means a mammal that is treated for a disease or condition. Patients are of, but not limited to, the following origin, human, ovine, porcine, equine, bovine, rabbit and the like.

The term "potency" in relation to FSH activity, refers to the ability of an FSH formulation or a mixed formulation, to elicit biological responses associated with FSH, such as ovarian weight gain in the Steelman-Pohley assay[8], or follicular growth in a female patient. Follicular growth in a female patient can be evaluated by ultrasound, for example, in terms of the number of follicles having a mean diameter of at or about 16 mm on day 8 of stimulation. Biological activity is evaluated with respect to an accepted standard for FSH.

The term "potency" in relation to LH activity, refers to the ability of an LH formulation or a mixed formulation, to elicit biological responses associated with LH, such as seminal vesicle weight gain method.[9] Biological activity of LH is evaluated with respect to an accepted standard for LH.

The term "aqueous diluent" refers to a liquid solvent that contains water. Aqueous solvent systems may be consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol.

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable isotonicity agents include, but are not limited to, amino acids or proteins (e.g., glycine or albumin), salts (e.g., sodium chloride), and sugars (e.g., dextrose, sucrose and lactose).

The term "bacteriostatic" or "bacteriostatic agent" refers to a compound or compostions added to a formulation to act as an anti bacterial agent. A preserved FSH or FSH variant or FSH and LH containing formulation of the present invention preferably meets statutory or regulatory guidelines for preservative effectiveness to be a commercially viable multi-use product, preferably in humans. Examples of bacteriostatics include phenol, m-cresol, m-cresol, o-cresol, chlorocresol, benzyl alcohol, alkylparaben (methyl, ethyl, propyl, butyl and the like), benzalkonium chloride, benzethonium chloride, sodium dehydroacetate and thimerosal.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are phosphate buffers with saline or an acceptable salt.

The term "phosphate buffer" refers to solutions containing phosphoric acid or salts thereof, adjusted to a desired pH. Generally phosphate buffers are prepared from phosphoric acid, or a sail of phosphoric acid, including but not limited to sodium and potassium salts. Several salts of phosphoric acid are known in the art, such as sodium and potassium monobasic, dibasic, and tribasic salts of the acid. Salts of phosphoric acid are also known to occur as hydrates of the occurring salt. Phosphate buffers may cover a range of pHs, such as from about pH 4 to about pH 10, and preferred ranges from about pH 5 to about pH 9, and a most preferred range of at or about 6.0 to at or about 8.0, most preferably at or about pH 7.0.

The term "vial" refers broadly to a reservoir suitable for retaining FSH in solid or liquid form in a contained sterile state. Examples of a vial as used herein include ampoules, cartridges, blister packages, or other such reservoir suitable for delivery of the FSH to the patient via syringe, pump (including osmotic), catheter, transdermal patch, pulmonary or transmucosal spray. Vials suitable for packaging products for parenteral, pulmonary, transmucosal, or transdermal administration are well known and recognized in the art.

The term "stability" refers to the physical, chemical, and conformational stability of FSH and LH in the formulations of the present invention (including maintenance of biological potency). Instability of a protein formulation may be caused by chemical degradation or aggregation of the protein molecules to form higher order polymers, by dissociation of the heterodimers into monomers, deglycosylation, modification of glycosylation, oxidation (particularly of the α-subunit) or any other structural modification that reduces at least one biological activity of an FSH polypeptide included in the present invention.

A "stable" solution or formulation, is one wherein the degree of degradation, modification, aggregation, loss of biological activity and the like, of proteins therein is acceptably controlled, and does not increase unacceptably with time. Preferably the formulation retains at least at or about 80% of the labelled FSH activity and at least at or about 80% of the labelled LH activity over a period of 6 months at a temperature of at or about 2-8° C., more preferably at or about 2-8° C., more preferably at or about 4-5° C. FSH activity can be measured using the Steelman-Pohley ovarian weight gain bioassay[5]. LH activity can be measured using the seminal vesicle weight gain bioassay[10].

The term "treating" refers to the administration, follow up, management and/or care of a patient for which FSH and/or LH administration is desirable for the purpose of follicle or testicular stimulation or any other physiological response regulated by FSH and/or LH. Treating can thus include, but is not limited to, the administration of FSH and/or LH for the induction or improvement of sperm quality, stimulation of testosterone release in the male, or follicular development or for ovulation induction in the female.

The expression "multi-dose use" is intended to include the use of a single vial, ampoule or cartridge of an FSH formulation or a formulation of FSH and LH for more than one injection, for example 2, 3, 4, 5, 6 or more injections. The injections are preferably made over a period of at least at or about 12 hours, 24 hours, 48 hours, etc., preferably up to a period of at or about 12 days. The injections may be spaced in time, for example, by a period of 6, 12, 24, 48 or 72 hours.

A "salt" of a protein is an acid or base addition salt. Such salts are preferably formed between any one or more of the charged groups in the protein and any one or more physiologically acceptable, non-toxic cations or anions. Organic and inorganic salts include, for example, those prepared from acids such as hydrochloric, sulphuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium.

The inventors have found that by formulating FSH and mixtures of FSH and LH with a surfactant selected from block copolymers of ethylene oxide and propylene oxide, preferably Pluronic® F77, Pluronic F87, Pluronic F88 and Pluronic® F68, particularly preferably Pluronic F68 (BASF, Pluronic F68 is also known as Poloxa mer 188) they obtain stable formulations that minimise the loss of active principle (FSH or FSH and LH) caused by adsorption on the surfaces of the vial and/or delivery device (e.g. syringe, pump, catheter, etc.).

The inventors have further found that by formulating FSH and mixtures of FSH and LH with a surfactant selected from block copolymers of ethylene oxide and propylene oxide, preferably Pluronic® F77, Pluronic F87, Pluronic F88 and Pluronic® F68, particularly preferably Pluronic F68 (BASF, Pluronic F68 is also known as Poloxamer 188) they obtain a stable formulation that avoids the problem of precipitation in the presence of a bacteriostatic agent, such as m-cresol and phenol. Precipitation, resulting in the formation of turbid or milky solutions occurs when TWEEN 20 is used with m-cresol or phenol.

The Pluronic surfactants are block copolymers of ethylene oxide (EO) and propylene oxide (PO). The propylene oxide block (PO) is sandwiched between two ethylene oxide (EO) blocks.

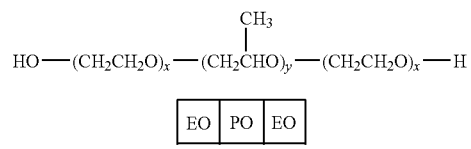

Pluronic surfactants are synthesised in a two-step process:

1. A hydrophobe of the desired molecular weight is created by the controlled addition of propylene oxide to the two hydroxyl groups of propylene glycol; and 2. Ethylene oxide is added to sandwich the hydrophobe between hydrophilic groups.

In Pluronic® F77, the percentage of polyoxyethylene (hydrophile) is 70%, and the molecular weight of the hydrophobe (polyoxypropylene) is approximately 2306 Da.

In Pluronic F87, the percentage of polyoxyethylene (hydrophile) is 70%, and the molecular weight of the hydrophobe (polyoxypropylene) is approximately 2,644 Da.

In Pluronic F88, the percentage of polyoxyethylene (hydrophile) is 80%, and the molecular weight of the hydrophobe (polyoxypropylene) is approximately 2,644 Da.

In Pluronic F68, the percentage of polyoxyethylene (hydrophile) is 80%, and the molecular weight of the hydrophobe (polyoxypropylene) is approximately 1,967 Da.

Typical properties of Pluronic F77 are listed below:

Average Molecular Weight 6600;

Melt/pour point 48° C.;

Physical Form @20° C.: solid;

Viscosity (Brookfield) cps: 480 [liquids at 25° C., pastes at 60° C. and solids at 77° C.];

Surface tension, dynes/cm@25° C.;
   0.1% Conc.: 47.0
   0.01% Conc.: 49.3
   0.001% Conc.: 52.8 interfacial tension, dynes/cm@25° C. vs. Nujol;
   0.1% Conc.: 17.7
   0.01% Conc.: 20.8
   0.01% Conc.: 25.5

Draves Wetting, Seconds 25° C.
   1.0% Conc.: >360
   0.1% Conc.: >360

Foam Height
   Ross Miles, 0.1%, mm@50° C.: 100
   Ross Miles, 0.1%, mm@26° C.: 47
   Dynamic, 0.1%, mm@400 ml/min: >600

Cloud point in aqueous solution, ° C.
   1% Conc.: >100
   10% Conc.: >100

HLB (hydrophile-lipophile balance): 25

Typical properties of Pluronic F87 are listed below:

Average Molecular Weight 7700;

Melt/pour point 49° C.;

Physical Form @20° C.: solid;

Viscosity (Brookfield) cps: 700 [liquids at 25° C., pastes at 60° C. and solids at 77° C.];

Surface tension, dynes/cm@25° C.;
   0.1% Conc.: 44.0
   0.01% Conc.: 47.0
   0.001% Conc.: 50.2

Interfacial tension, dynes/cm@25° C. vs Nujol;
   0.1% Conc.: 17.4
   0.01% Conc.: 20.3
   0.01% Conc.: 23.3

Draves Wetting, Seconds 25° C.
   1.0% Conc.: >360
   0.1% Conc.: >360

Foam Height
   Ross Miles, 0.1%, mm@50° C.: 80
   Ross Miles, 0.1%, mm@26° C.: 37
   Dynamic, 0.1%, mm@400 ml/min: >600

Cloud point in aqueous solution, ° C.
   1% Conc.: >100
   10% Conc.: >100

HLB (hydrophile-lipophile balance): 24

Typical properties of Pluronic F88 are listed below:

Average Molecular Weight 11400;

Melt/pour point 54° C.;

Physical Form @20° C.: solid;

Viscosity (Brookfield) cps: 2300 [liquids at 25° C., pastes at 60° C. and solids at 77° C.];

Surface tension, dynes/cm@25° C.;
   0.1% Conc.: 48.5
   0.01% Conc.: 52.6
   0.001% Conc.: 55.7

Interfacial tension, dynes/cm@25° C. vs Nujol;
   0.1% Conc.: 20.5
   0.01% Conc.: 23.3
   0.01% Conc.: 27.0

Draves Wetting, Seconds 25° C.
   1.0% Conc.: >360
   0.1% Conc.: >360

Foam Height
   Ross Miles, 0.1%, mm@50° C.: 80
   Ross Miles, 0.1%, mm@26° C.: 37
   Dynamic, 0.1%, mm@400 ml/min: >600

Cloud point in aqueous solution, ° C.
   1% Conc.: >100
   10% Conc.: >100

HLB (hydrophile-lipophile balance): 28

Typical properties of Pluronic F68 are listed below:

Average Molecular Weight 8400;

Melt/pour point 52° C.;

Physical Form @20° C.: solid:

Viscosity (Brookfield) cps: 1000 [liquids at 25° C., pastes at 60° C. and solids at 77° C.];

Surface tension, dynes/cm@25° C.;
   0.1% Conc.: 50.3
   0.01% Conc.: 51.2
   0.001% Conc.: 53.6

Interfacial tension, dynes/cm@25° C. vs Nujol;
   0.1% Conc.: 19.8
   0.01% Conc.: 24.0
   0.01% Conc.: 26.0

Draves Wetting, Seconds 25° C.
   1.0% Conc.: >360
   0.1% Conc.: >360

Foam Height
   Ross Miles, 0.1%, mm@50° C.: 35
   Ross Miles, 0.1%, mm@26° C.: 40
   Dynamic, 0.1%, mm@400 ml/min: >600

Cloud point in aqueous solution, ° C.
   1% Conc.: >100
   10% Conc.: >100

HLB (hydrophilelipophile balance): 29

Other polymers having properties similar to those listed above may also be used in the formulations of the invention. The preferred surfactant is Pluronic F68, and surfactants having similar properties.

Pluronic, particularly Pluronic F68, is preferably present in the formulation at a concentration that is sufficient to maintain FSH and/or LH stability over the desired storage period (for example 6 to 12 to 24 months), and also at a concentration that is sufficient to prevent protein losses due to adsorption on surfaces, such as the vial, ampoule or cartridge or the syringe.

Preferably the concentration of Pluronic, particularly Pluronic F68, in liquid formulations is at or about 0.01 mg/ml to at or about 1 mg/ml, more preferably at or about 0.05 mg/ml to at or about 0.5 mg/ml, more particularly preferably at or about 0.2 mg/ml to at or about 0.4 mg/ml, most preferably at or about 0.1 mg/ml.

The follicle-stimulating hormone (FSH) within the freeze-dried formulation is preferably present at a concentration (w/w) of at or about 0.1 to 10 µg/mg of the total formulation. In one embodiment the follicle-stimulating hormone (FSH) is present at a concentration of at or about 0.3 to 5 µg/mg of the total formulation. In a further embodiment the follicle-stimulating hormone (FSH) is present at a concentration of at or about 0.37 to 2 µg/mg of the total formulation.

The luteinising hormone (LH) within the freeze-dried formulation is preferably present at a concentration of at or about 0.1 to 3 µg/mg of the total formulation. In one embodiment, the luteinising hormone (LH) is present at a concentration of at or about 0.1 to 1 µg/mg of the total formulation. In a further embodiment the luteinising hormone (LH) is present at a concentration of at or about 0.1 to 0.6 µg/mg of the total formulation.

In the liquid formulations—including the reconstituted formulations—comprising FSH, preferably the concentration of FSH in the formulation is at or about 150 IU/ml to at or about 2,000 IU/ml, more preferably at or about 300 IU/ml to at or about 1,500 IU/ml, more particularly preferably at or about 450 to at or about 750, most preferably at or about 600 IU/ml.

In the liquid formulations—including the reconstituted formulations—comprising LH, preferably the LH concentration in the formulation is at or about 50 IU/ml to at or about 2,000 IU/ml, more preferably at or about 150 to at or about 1,500 IU/ml, more particularly preferably at or about 300 IU/ml to at or about 750 IU/ml, particularly preferably 626 IU/ml.

In formulations comprising both FSH and LH, the ratio of FSH to LH (FSH:LH, IU:IU, FSH measured with rat ovarian weight gain assay and LH measured with rat seminal vesicle weight gain assay) is preferably within the range of at or about 6:1 to at or about 1:6, more preferably at or about 4:1 to at or about 1:2, more particularly preferably at or about 3:1 to at or about 1:1. Particularly preferred ratios are 1:1 and 2:1.

In the freeze dried formulations, the surfactant e.g. Pluronic F 68, is preferably present at a concentration of at or about 0.001 to at or about 0.1 mg per mg of the total formulation, more preferably at or about 0.01 to at or about 0.075 mg/mg.

Preferably the concentration of Pluronic, particularly Pluronic F68, in the reconstituted formulations is at or about 0.01 mg/ml to at or about 1 mg/ml, more preferably at or about 0.05 mg/ml to at or about 0.5 mg/ml, more particularly preferably at or about 0.2 mg/ml to at or about 0.4 mg/ml, most preferably at or about 0.1 mg/ml.

Preferably the FSH and LH are produced recombinantly, particularly preferably they are produced in Chinese hamster ovary cells transfected with a vector or vectors comprising DNA coding for the human glycoprotein alpha-subunit and the beta-subunit of FSH or LH. DNA encoding the alpha and beta-subunits may be present on the same or different vectors.

Recombinant FSH and LH have several advantages over their urinary counterparts. Culture and isolation techniques using recombinant cells permit consistency between batches. In contrast, urinary FSH and LH vary greatly from batch to batch in such characteristics as purity, glycosylation pattern, sialyation and oxidation of the subunits. Due to greater batch-to-batch consistency and purity of recombinant FSH and LH, the hormones can be readily identified and quantified using techniques such as isoelectric focussing (IEF). The ease with which recombinant FSH and LH can be identified and quantified permits the filling of vials by mass of hormone (fill-by-mass) rather than filling by bioassay.

Preferably formulations of FSH of the present invention have pH between at or about 6.0 and at or about 8.0, more preferably at or about 6.8 to at or about 7.8, including about pH 7.0, pH 7.2 and 7.4, A preferred buffer is phosphate, with preferred counterions being sodium or potassium ions. Phosphate saline buffers are well known in the art, such as Dulbecco's Phosphate buffered saline. Buffer concentrations in total solution can vary between at or about 5 mM, 9.5 mM, 10 mM, 50 mM, 100 mM, 150 mM, 200 mM, 250 mM, and 500 mM. Preferably the buffer concentration is at or about 10 mM. Particularly preferred is a buffer 10 mM in phosphate ions with a pH of 7.0.

Preferably formulations of mixtures of FSH and LH of the present invention have pH between at or about 6.0 and at or about 9.0, more preferably at or about 6.8 to at or about 8.5, including about pH 7.0, pH 8.0, and 8.2, most preferably at or about pH 8.0.

The invention is directed to liquid formulations as well as freeze dried (lyophilised) formulations that may be reconstituted, in which the solvent (also for reconstitution) is water for injection. Liquid formulations may be single dose or multi-dose. Those liquid as well as freeze dried FSH and/or LH formulations of the invention that are intended for multi-dose use preferably comprise a bacteriostatic, such as phenol, m-cresol, p-cresol, o-cresol, chlorocresol, benzyl alcohol, alkylparaben (methyl, ethyl, propyl, butyl and the like), thymol, benzalkonium chloride, benzethonium chloride, sodium dehydroacetate and thimerosal. Particularly preferred are phenol, benzyl alcohol and m-cresol, more preferred are phenol and m-cresol, most preferred is m-cresol. The bacteriostatic agent is used in an amount that will yield a concentration that is effective to maintain the formulation essentially bacteria free (suitable for injection) over the multi-dose injection period, which may be at or about 12 or 24 hours to at or about 12 or 14 days, preferably at or about 6 to at or about 12 days. The bacteriostatic is preferably present in a concentration of at or about 0.1% (mass bacteriostatic/mass of solvent) to at or about 20%, more preferably at or about 0.2% to at or about 1.0%. In the case of benzyl alcohol, particularly preferred is a concentration of 0.9%). In the case of phenol, particularly preferred is at or about 0.5%. In the case of m-cresol, particularly preferred is a concentration of at or about 0.3% (e.g. at or about 3 mg/ml in WFI).

In a preferred embodiment, the invention provides a liquid pharmaceutical composition, preferably for multi-dose use, comprising FSH or a variant thereof, a surfactant selected from Pluronic® F77, Pluronic F87, Pluronic F88 and Pluronic F68, and a bacteriostatic selected from m-cresol and phenol, preferably m-cresol.

In a further preferred embodiment, the invention provides a liquid pharmaceutical composition, preferably for multi-dose use, comprising LH, a surfactant selected from Pluronic® F77, Pluronic F87, Pluronic F88 and Pluronic F68, and a bacteriostatic selected from m-cresol and phenol, preferably m-cresol.

In a further preferred embodiment, the invention provides a liquid pharmaceutical composition, preferably for multi dose use, comprising FSH and LH, a surfactant selected from Pluronic® F77, Pluronic F87, Pluronic F88 and Pluronic F68, and a bacteriostatic selected from m-cresol and phenol, preferably m-cresol. Preferably the FSH and LH are present in a ratio (FSH:LH) of at or about 2:1 to at or about 1:1.

In a further preferred embodiment, the invention provides a method for manufacturing a liquid pharmaceutical composition, preferably for multi-dose use, comprising forming an aqueous solution of FSH or a variant thereof, a surfactant selected from Pluronic® F77, Pluronic F87, Pluronic F88 and Pluronic F68, and a bacteriostatic selected from m-cresol and phenol, preferably m-cresol, and WFI.

In a further preferred embodiment, the invention provides a method for manufacturing a liquid pharmaceutical composition, preferably for multi-dose use, comprising forming an aqueous solution of LH, a surfactant selected from Pluronic® F77, to Pluronic F87, Pluronic F88 and Pluronic F68, and a bacteriostatic selected from m-cresol and phenol, preferably m-cresol, and WFI.

In a further preferred embodiment, the invention provides a method for manufacturing a liquid pharmaceutical composition, preferably for mufti-dose use, comprising forming an aqueous solution of FSH and LH, a surfactant selected from Pluronic® F77, Pluronic F87, Pluronic F88 and Pluronic F68, and a bacteriostatic selected from m-cresol and phenol, preferably m-cresol, and WFI.

In yet another preferred embodiment the invention provides a method for manufacturing a packaged pharmaceutical composition comprising dispensing a solution comprising FSH, a surfactant selected from Pluronic® F77, Pluronic F87, Pluronic F88 and Pluronic F68, and a bacteriostatic selected from m-cresol and phenol, preferably m-cresol.

In yet another preferred embodiment the invention provides a method for manufacturing a packaged pharmaceutical composition comprising dispensing a solution comprising FSH and LH, a surfactant selected from Pluronic® F77, Pluronic F87, Pluronic F88 and Pluronic F68, and a bacteriostatic selected from m-cresol and phenol, preferably m-cresol.

In yet another preferred embodiment the invention provides an article of manufacture for human pharmaceutical use, comprising a vial comprising a solution of FSH or an FSH variant, a surfactant selected from Pluronic® F77, Pluronic F87, Pluronic F88 and Pluronic® F88, and a bacteriostatic selected from m-cresol and phenol, preferably m-cresol, and written material stating that such solution may be held over a period of at or about twenty-four hours or greater after the first use.

Preferably the written material states that the solution may be held up to at or about 12 or 14 days after the first use.

In yet another preferred embodiment the invention provides an article of manufacture for human pharmaceutical use, comprising a vial comprising a solution of FSH and LH, a surfactant selected from Pluronic® F77, Pluronic F87, Pluronic F88 and Pluronic F68, and a bacteriostatic selected from m-cresol and phenol, preferably m-cresol, and written material stating that such solution may be held over a period of at or about twenty-four hours or greater after the first use. Preferably the written material states that the solution may be held up to at or about 12 or 14 days after the first use.

In a particularly preferred embodiment, the formulation comprises m-cresol and Pluronic F68. The inventors have surprisingly found that formulations comprising Pluronic F68 do not precipitate in the presence of m-cresol, a problem observed with other surfactants.

Before the first use, that is before the seal of the vial ampoule or cartridge has been broken, the formulations of the invention may be kept for at least at or about 6 months, 12 months or 24 months. Under preferred storage conditions, before the first use, the formulations are kept away from bright light (preferably in the dark), at temperatures of at or about 2-8° C., more preferably at or about 4-5° C.

In a specific embodiment the invention provides a freeze dried formulation for reconstitution, preferably for multi-dose use, comprising FSH or a variant thereof and a surfactant selected from Pluronic® F77, Pluronic F87, Pluronic F88 and Pluronic F68, preferably Pluronic F68.

In a further specific embodiment the invention provides a freeze dried formulation for reconstitution, preferably for multi-dose use, comprising LH, a surfactant selected from Pluronic® F77, Pluronic F87, Pluronic F88 and Pluronic F68, preferably Pluronic F68.

In a further specific embodiment, the invention provides a freeze dried formulation, preferably for multi-dose use, comprising FSH and LH, a surfactant selected from Pluronic® F77, Pluronic F87, Pluronic F88 and Pluronic F68, preferably Pluronic F68.

Preferably the FSH and LH are present in a ratio (FSH:LH) of at or about 2:1 to at or about 1:1.

In a further specific embodiment, the invention provides a method for manufacturing a freeze dried formulation, preferably for multi-dose use after reconstitution, comprising forming a mixture of FSH or a variant thereof with a surfactant selected from Pluronic® F77, Pluronic F87, Pluronic F88 and Pluronic® F68, and subjecting said mixture to lyophilisation.

In a further specific embodiment, the invention provides a method for manufacturing a freeze dried formulation, preferably for multi-dose use after reconstitution, comprising forming a mixture of LH with a surfactant selected from Pluronic F77, Pluronic F87, Pluronic F88 and Pluronic F68, and subjecting said mixture to lyophilisation.

In a further specific embodiment the invention provides a method for manufacturing a freeze dried formulation preferably for multi-dose use after reconstitution, comprising forming a mixture of FSH and LH as well as a surfactant selected from Pluronic® F77, Pluronic F87, Pluronic F88 and Pluronic F68, and subjecting said mixture to lyophilisation.

In yet another preferred embodiment, the invention provides a method for manufacturing a packaged pharmaceutical composition comprising dispensing a freeze dried mixture comprising FSH and a surfactant selected from Pluronic® F77, Pluronic F87, Pluronic F88 and Pluronic F68.

In yet another preferred embodiment, the invention provides a method for manufacturing a packaged pharmaceutical composition comprising dispensing a freeze dried mixture comprising LH and a surfactant selected from Pluronic® F77, Pluronic F87, Pluronic F88 and Pluronic F68 into a container.

In yet another preferred embodiment, the invention provides a method for manufacturing a packaged pharmaceutical composition comprising dispensing a freeze dried mixture comprising FSH as well as LH and a surfactant selected from Pluronic® F77, Pluronic F87, Pluronic F88 and Pluronic F68 into a container.

In yet another preferred embodiment, the invention provides an article of manufacture for human pharmaceutical use, comprising a first container or vial comprising freeze dried FSH or an FSH variant and a surfactant selected from Pluronic® F77, Pluronic F87, Pluronic F88 and Pluronic F68. A second container or vial contains a diluent for reconstitution, preferably water and a bacteriostatic selected from m-cresol and phenol, preferably m-cresol.

In yet another preferred embodiment, the invention provides an article of manufacture for human pharmaceutical use, comprising a first container or vial comprising freeze dried LH or an LH variant and a surfactant selected from Pluronic® F77, Pluronic F87, Pluronic F88 and Pluronic F68. A second container or vial contains a diluent for reconstitution, preferably water and a bacteriostatic selected from m-cresol and phenol, preferably m-cresol.

In yet another preferred embodiment, the invention provides an article of manufacture for human pharmaceutical use, comprising a first container or vial comprising freeze dried FSH or an FSH variant as well as LH or an LH variant and a surfactant selected from Pluronic® F77, Pluronic F87, Pluronic F88 and Pluronic F68. A second container or vial contains a diluent for reconstitution, preferably water and a bacteriostatic selected from m-cresol and phenol, preferably m-cresol.

In a particularly preferred embodiment, the solvent for reconstitution comprises m-cresol. The inventors have found that freeze dried formulations comprising Pluronic F68 do not precipitate when reconstituted with a diluent containing m-cresol, a problem observed with other surfactants, e.g. Tween.

The freeze dried formulations of the invention may be kept for at least at or about 6 months, 12 months or 24 months. Under preferred storage conditions, before the first use, the formulations are kept away from bright light (preferably in the dark), at temperatures of at or about 25, preferably of at or about 2-8° C., more preferably at or about 4-5° C.

After the first use of a liquid or a reconstituted multi-dose formulation it may be kept and used for at least at or about 24 hours, preferably at least at or about 4, 5 or 6 days, more preferably for up to 12 or 14 days. After the first use the formulation is preferably stored at below room temperature (i.e. below at or about 25° C.), more preferably below at or about 10° C., more preferably at or about 2-8° C., most preferably at or about 5-0° C.

Preferably the formulations of the invention contain an antioxidant such as methionine, sodium bisulfite, salts of ethylenediaminetetraacetic acid (EDTA), butylated hydroxytoluene (BHT), and butylated hydroxy anisole (BHA). Most preferred is methionine. The antioxidant prevents oxidation of FSH and LH (particularly the α-subunit).

Methionine in the liquid and/or reconstituted formulation is preferably present at a concentration of at or about 0.01 to at or about 1.0 mg/ml, more preferably at or about 0.05 to at or about 0.5 mg/ml, most preferably at or about 0.1 mg/ml.

Preferably the formulations of the invention contain a mono- or disaccharide or a sugar alcohol as stabiliser and tonicity adjusting agent, such as sucrose, dextrose, lactose, mannitol and/or glycerol. Most preferred is sucrose, preferably at a concentration of at or about 60 mg/ml.

As noted above, the invention provides liquid formulations for single use and multi-dose use, containing a bacteriostatic, or to which a bacteriostatic is added when the formulation is reconstituted. The formulations of the invention are suitable for pharmaceutical or veterinary use.

As noted above, in a preferred embodiment, the invention provides an article of manufacture, comprising packaging material and a vial comprising a solution of FSH or an FSH variant LH, or FSH and LH, Pluronic F68 and a bacteriostatic selected from phenol and m-cresol, optionally with butters and/or other excipients, in an aqueous diluent wherein said packaging material comprises written material which indicates that such solution may be held over a period of twenty-four hours or greater after the first use. The invention further comprises an article of manufacture, comprising packaging material, a vial comprising a formulation of FSH or an FSH variant according to the invention, wherein said packaging material comprises written material which instructs a patient to reconstitute the FSH or an FSH variant in the aqueous diluent to form a solution which may be held over a period of twenty-four hours or greater.

As noted above, in a preferred embodiment, the invention provides an article of manufacture, comprising packaging material and a vial comprising freeze dried FSH or an FSH variant, LH or an LH variant, or FSH and LH, Pluronic F68. The bacteriostatic within the second container including the diluent is selected from phenol and m-cresol, optionally with further excipients, wherein said packaging material comprises written material which indicates that such solution may be held over a period of twenty-four hours or greater after the first use.

The range of protein hormone in the formulations of the invention includes amounts yielding upon reconstitution, concentrations from about 1.0 µg/ml to about 50 mg/ml, although lower and higher concentrations are operable and are dependent on the intended delivery vehicle, e.g., solution formulations will differ from transdermal patch, pulmonary, transmucosal, or osmotic or micro pump methods. The protein hormone concentration is preferably at or about 5.0 µg/ml to at or about 2 mg/ml, more preferably at or about 10 µg/ml to at or about 1 mg/ml, most preferably at or about 50 µg/ml to at or about 200 µg/ml.

The range of protein hormone in the formulations of the invention includes amounts yielding upon reconstitution, concentrations from about 1.0 µg/ml to about 50 mg/ml, although lower and higher concentrations are operable and are dependent on the intended delivery vehicle, e.g., solution formulations will differ from transdermal patch, pulmonary, transmucosal, or osmotic or micro pump methods. The protein hormone concentration is preferably at or about 5.0 µg/ml to at or about 2 mg/ml, more preferably at or about 10 µg/ml to at or about 1 mg/ml, most preferably at or about 50 µg/ml to at or about 200 µg/ml.

Preferably the formulations of the invention retain at least at or about 80% of the FSH activity and/or LH activity at the time of packaging over a period of 24 months (before the first use). FSH activity can be measured using the Steelman-Pohley ovarian weight gain bioassay[5]. LH activity can be measured using the rat seminal vesicle weight gain bioassay.

The liquid formulations of the present invention can be prepared by a process which comprises mixing FSH or an FSH variant, LH, or a mixture of FSH and LH and Pluronic F68 and a bacteriostatic selected from phenol and m-cresol as solids or dissolving FSH or an FSH variant, LH, or a mixture of FSH and LH ("protein") and Pluronic F68 and a bacteriostatic selected from phenol and m-cresol in an aqueous diluent. Mixing the components and dissolving them in an aqueous diluent is carried out using conventional dissolution and mixing procedures. To prepare a suitable formulation, for example, a measured amount of FSH or FSH variant, LH or a mixture of FSH and LH in buffered solution is combined with Pluronic F68 and a bacteriostatic selected from phenol and m-cresol in a buffered solution in quantities sufficient to provide the protein, Pluronic F68 and the bacteriostatic at the desired concentrations. The resulting solution is then dispensed into vials, ampoules or cartridges. Variations of this process would be recognized by one of ordinary skill in the art. For example, the order the components are added, whether additional additives are used, the temperature and pH at which the formulation is prepared, are all factors that may be optimised for the concentration and means of administration used.

In a preferred embodiment the liquid formulations of the invention are made by preparing individual stock solutions of known concentration of all the components of the formulation (e.g. buffer sodium phosphate, sucrose, TWEEN, methionine, FSH and/or LH), and aliquoting volumetric amounts to form a mother solution of the same composition as the final formulation. The mother solution is preferably filtered through a Duropore® (Millipore) 0.22 micron PDF membrane, to remove microorganisms, and then aliquots are dispensed into individual containers, such as vials, ampoules or cartridges.

The freeze dried formulations of the present invention can be prepared by a process which comprises mixing FSH or an FSH variant LH or an FSH variant or a mixture of FSH and LH and Pluronic F68 as well as further excipients like an antioxidant and/or a buffer and subjecting the mixture to a lyophilisation. Mixing the components and lyophilising them is carried out using conventional procedures. To prepare a suitable formulation, for example, a measured amount of FSH or FSH variant, LH or LH variant or a mixture of FSH and LH is combined with Pluronic F68 and the resulting mixture is lyophilized and then dispensed into vials, ampoules or cartridges. Variations of this process would be recognized by one of ordinary skill in the art. For example, the order the components are added, whether additional additives are used, the temperature and pH at which the formulation is prepared, are all factors that may be optimised for the concentration and means of administration used.

The formulations of the invention can be administered using recognized devices. Examples comprising these single vial systems include pen-injector devices for delivery of a solution such as EasyJect®, Gonal-F® Pen, Humaject®, NovoPen®, B-D®Pen, AutoPen®, and OptiPen®.

The products presently claimed include packaging material. The packaging material provides, in addition to the information required by the regulatory agencies, the conditions under which the product may be used. The packaging material of the present invention provides instructions to the patient to reconstitute the FSH or an FSH variant in the aqueous diluent to form a solution and to use the solution over a period of twenty-four hours or greater for the two vial, wet/dry, product. For the single vial, solution product the label indicates that such solution may be stored after first use for a period of twenty-four hours or greater, preferably for up to 12 or 14 days. The presently claimed products are useful for human pharmaceutical product use.

The stable preserved formulations may be provided to patients as clear solutions. The solution may be for single use or it may be reused multiple times and may suffice for a single or multiple cycles of patient treatment and thus provides a more convenient treatment regimen than currently available.

FSH or an FSH variant LH, or mixtures of FSH and LH in either the stable or preserved formulations or solutions described herein, may be adminstered to a patient in accordance with the present invention via a variety of delivery methods including SC or IM injection; transdermal, pulmonary, transmucosal, implant osmotic pump cartridge, micro pump, oral, or other means appreciated by the skilled artisan, as well-known in the art.

The following examples are provided merely to further illustrate the preparation of the formulations and compositions of the invention. The scope of the invention shall not be construed as merely consisting of the following examples.

Example 1

Comparative Formulations

Materials

| Item | Manufacturer |
| --- | --- |
| r-hFSH Bulk used for candidate formulations | Laboratoires Serono SA |
| D-Mannitol (DAB, Ph Eur, BP, FU, USP, FCC, E421) | Merck |
| Sucrose (DAB, Ph Eur, BP, NF) | Merck |
| NaCl (ACS, ISO) | Merck |
| $Na_2HPO_4 2H_2O$ (GR for analysis) | Merck |
| $NaH_2PO_4 H_2O$ (GR for analysis) | Merck |
| Benzyl Alcohol (GR for analysis) | Merck |
| m-Cresol (for synthesis) | Merck |
| TWEEN 20 (Polysorbate 20) (for synthesis) | Merck |
| Pluronic F68 (Poloxamer 188) | Sigma |
| I-Methionine (for biochemistry) | Merck |
| Ortho-phosphoric Acid 85% (Ph Eur, BP, NF) | Merck |
| 1.5 mL glass cartridge | SFAM (siliconed at Aguettant) |
| Rubbers Type A | West Company |
| Crim caps | Aguettant |
| Millex-GV Syringe Driven Filter Unit - Durapore | Millipore |
| Durapore Membrane Filters 0.22 μm GV | Millipore |
| 20 mL Plastic syringe Plastipak | Becton Dickinson |
| Steel Holder for filtration | Sartorius |

Equipment

| | | | |
| --- | --- | --- | --- |
| HPLC Systems | Detector mod. 486 or 490 Controller mod. 600S Pump mod. 626 Autosampler mod. 717 | Waters | 2 |
| pH meter | Mod. 654 | Metrohm | 1 |
| Osmometer | 030-D | Osmomat | 1 |

The following study evaluated the following parameters for a large number of formulations:

Compatibility of surfactant and bacteriostatic

Oxidation of alpha-subunit

The formulations were multi-dose formulations and contained either TWEEN 20 or Pluronic F68 as well as a bacteriostatic agent. The following three bacteriostatic agents were evaluated:

Benzyl alcohol 0.9% m-Cresol 0.3%

Phenol 0.5%

TWEEN 20 and Pluronic F68 were used at the following range of concentrations:

TWEEN 20: range from 10 to 100 μg/g

Pluronic F68: range from 10 to 100 μg/g

Solutions prepared are listed in Table 1.

TABLE 1

Comparative formulations

| ID # | Na$_2$HPO$_4$2H$_2$O (mg/g) | NaH$_2$PO$_4$H$_2$O (mg/g) | r-hFSH* | Pluronic F68 (µg/g) | TWEEN 20 (µg/g) | Bacteriostat | Excipient (mg/g) |
|---|---|---|---|---|---|---|---|
| 1P | 1.11 | 0.45 | 600 IU/g | 10 | — | 0.5% Phenol | Sucrose 70.6 |
| 2P | 1.11 | 0.45 | 600 IU/g | 10 | — | 0.5% Phenol | Mannitol 38.7 |
| 3P | 1.11 | 0.45 | 600 IU/g | 100 | — | 0.5% Phenol | Sucrose 70.6 |
| 4P | 1.11 | 0.45 | 600 IU/g | 100 | — | 0.5% Phenol | Mannitol 38.7 |
| 5P | 1.11 | 0.45 | 600 IU/g | — | 10 | 0.5% Phenol | Sucrose 70.6 |
| 6P | 1.11 | 0.45 | 600 IU/g | — | 10 | 0.5% Phenol | Mannitol 38.7 |
| 7 | 1.11 | 0.45 | 600 IU/g | — | 100 | 0.9% benzyl alcohol | NaCl 6.0 |
| 8 | 1.11 | 0.45 | 600 IU/g | — | 100 | 0.9% benzyl alcohol | Sucrose 62.3 |
| 9 | 1.11 | 0.45 | 600 IU/g | — | 100 | 0.9% benzyl alcohol | Mannitol 34.1 |
| 10 | 1.11 | 0.45 | 600 IU/g | — | 100 | 0.3% m-Cresol | NaCl 7.6 |
| 11 | 1.11 | 0.45 | 600 IU/g | — | 100 | 0.3% m-Cresol | Sucrose 78.0 |
| 12 | 1.11 | 0.45 | 600 IU/g | — | 100 | 0.3% m-Cresol | Mannitol 42.7 |
| 13 | 1.11 | 0.45 | 600 IU/g | — | 10 | 0.9% benzyl alcohol | NaCl 6.0 |
| 14 | 1.11 | 0.45 | 600 IU/g | — | 10 | 0.9% benzyl alcohol | Sucrose 62.3 |
| 15 | 1.11 | 0.45 | 600 IU/g | — | 10 | 0.9% benzyl alcohol | Mannitol 34.1 |
| 16 | 1.11 | 0.45 | 600 IU/g | — | 10 | 0.3% m-Cresol | NaCl 7.6 |
| 17 | 1.11 | 0.45 | 600 IU/g | — | 10 | 0.3% m-Cresol | Sucrose 78.0 |
| 18 | 1.11 | 0.45 | 600 IU/g | — | 10 | 0.3% m-Cresol | Mannitol 42.7 |
| 19 | 1.11 | 0.45 | 600 IU/g | 100 | — | 0.9% benzyl alcohol | NaCl 6.0 |
| 20 | 1.11 | 0.45 | 600 IU/g | 100 | — | 0.9% benzyl alcohol | Sucrose 62.3 |
| 21 | 1.11 | 0.45 | 600 IU/g | 100 | — | 0.9% benzyl alcohol | Mannitol 34.1 |
| 22 | 1.11 | 0.45 | 600 IU/g | 100 | — | 0.3% m-Cresol | NaCl 7.6 |
| 23 | 1.11 | 0.45 | 600 IU/g | 100 | — | 0.3% m-Cresol | Sucrose 78.0 |
| 24 | 1.11 | 0.45 | 600 IU/g | 100 | — | 0.3% m-Cresol | Mannitol 42.7 |
| 25 | 1.11 | 0.45 | 600 IU/g | 10 | — | 0.9% benzyl alcohol | NaCl 6.0 |
| 26 | 1.11 | 0.45 | 600 IU/g | 10 | — | 0.9% benzyl alcohol | Sucrose 62.3 |
| 27 | 1.11 | 0.45 | 600 IU/g | 10 | — | 0.9% benzyl alcohol | Mannitol 34.1 |
| 28 | 1.11 | 0.45 | 600 IU/g | 10 | — | 0.3% m-Cresol | NaCl 7.6 |
| 29 | 1.11 | 0.45 | 600 IU/g | 10 | — | 0.3% m-Cresol | Sucrose 78.0 |
| 30 | 1.11 | 0.45 | 600 IU/g | 10 | — | 0.3% m-Cresol | Mannitol 42.7 |

*FSH was added to the formulations on the basis of its biopotency instead of protein content.

From visual examination of the formulations, it was determined that TWEEN 20 cannot be used with m-cresol and phenol because FSH formulations containing TWEEN 20 and m-cresol or TWEEN 20 and phenol presented a white opalescent suspension. In contrast, FSH formulations containing Pluronic F68 did not exhibit this problem with m-cresol and phenol. The use of Pluronic F68 permits the use of phenol and m-cresol.

Combination of FSH and Pluronic F68 with Antioxidants

The following antioxidants were evaluated for their ability to inhibit oxidation of the α-subunit in the presence of Pluronic F68:

Methionine: range from 10 to 100 µg/g
Ascorbic Acid: range from 10 to 100 µg/g

Sucrose and Mannitol were used as tonicity agents and TWEEN 20 or Pluronic were added at the concentration of 100 µg/g.

The formulations prepared are listed in Table 2.

TABLE 2

Comparative formulations with and without methionine

| ID# | $Na_2HPO_4 2H_2O$ (mg/g) | $NaH_2PO_4 H_2O$ (mg/g) | RhFSH | Pluronic F68 (µg/g) | TWEEN (µg/g) | Ascorbic Acid (µg/g) | Methionine (µg/g) | Bacteriostat | Excipient |
|---|---|---|---|---|---|---|---|---|---|
| 31 | 1.11 | 0.45 | 600 IU/g | 100 | — | — | — | 0.3% m-cresol | Sucrose |
| 32 | 1.11 | 0.45 | 600 IU/g | 100 | — | — | — | 0.3% m-cresol | Mannitol |
| 33 | 1.11 | 0.45 | 600 IU/g | — | 100 | — | — | 0.9% benzyl alcohol | Sucrose |
| 34 | 1.11 | 0.45 | 600 IU/g | — | 100 | — | — | 0.9% benzyl alcohol | Mannitol |
| 35 | 1.11 | 0.45 | 600 IU/g | 100 | — | — | — | 0.9% benzyl alcohol | Sucrose |
| 36 | 1.11 | 0.45 | 600 IU/g | 100 | — | — | — | 0.9% benzyl alcohol | Mannitol |
| 37 | 1.11 | 0.45 | 600 IU/g | 100 | — | — | 10 | 0.3% m-cresol | Sucrose |
| 38 | 1.11 | 0.45 | 600 IU/g | 100 | — | — | 10 | 0.3% m-cresol | Mannitol |
| 39 | 1.11 | 0.45 | 600 IU/g | 100 | — | — | 100 | 0.3% m-cresol | Sucrose |
| 40 | 1.11 | 0.45 | 600 IU/g | 100 | — | — | 100 | 0.3% m-cresol | Mannitol |
| 41 | 1.11 | 0.45 | 600 IU/g | 100 | — | 10 | — | 0.3% m-cresol | Sucrose |
| 42 | 1.11 | 0.45 | 600 IU/g | 100 | — | 10 | — | 0.3% m-cresol | Mannitol |
| 43 | 1.11 | 0.45 | 600 IU/g | 100 | — | 100 | — | 0.3% m-cresol | Sucrose |
| 44 | 1.11 | 0.45 | 600 IU/g | 100 | — | 100 | — | 0.3% m-cresol | Mannitol |
| 45 | 1.11 | 0.45 | 600 IU/g | — | 100 | — | 10 | 0.9% benzyl alcohol | Sucrose |
| 46 | 1.11 | 0.45 | 600 IU/g | — | 100 | — | 10 | 0.9% benzyl alcohol | Mannitol |
| 47 | 1.11 | 0.45 | 600 IU/g | — | 100 | — | 100 | 0.9% benzyl alcohol | Sucrose |
| 48 | 1.11 | 0.45 | 600 IU/g | — | 100 | — | 100 | 0.9% benzyl alcohol | Mannitol |
| 49 | 1.11 | 0.45 | 600 IU/g | — | 100 | 10 | — | 0.9% benzyl alcohol | Sucrose |
| 50 | 1.11 | 0.45 | 600 IU/g | — | 100 | 10 | — | 0.9% benzyl alcohol | Mannitol |
| 51 | 1.11 | 0.45 | 600 IU/g | — | 100 | 100 | — | 0.9% benzyl alcohol | Sucrose |
| 52 | 1.11 | 0.45 | 600 IU/g | — | 100 | 100 | — | 0.9% benzyl alcohol | Mannitol |
| 53 | 1.11 | 0.45 | 600 IU/g | 100 | — | — | 10 | 0.9% benzyl alcohol | Sucrose |
| 54 | 1.11 | 0.45 | 600 IU/g | 100 | — | — | 10 | 0.9% benzyl alcohol | Mannitol |
| 55 | 1.11 | 0.45 | 600 IU/g | 100 | — | — | 100 | 0.9% benzyl alcohol | Sucrose |
| 56 | 1.11 | 0.45 | 600 IU/g | 100 | — | — | 100 | 0.9% benzyl alcohol | Mannitol |
| 57 | 1.11 | 0.45 | 600 IU/g | 100 | — | 10 | — | 0.9% benzyl alcohol | Sucrose |
| 58 | 1.11 | 0.45 | 600 IU/g | 100 | — | 10 | — | 0.9% benzyl alcohol | Mannitol |
| 59 | 1.11 | 0.45 | 600 IU/g | 100 | — | 100 | — | 0.9% benzyl alcohol | Sucrose |

TABLE 2-continued

Comparative formulations with and without methionine

| ID# | Na$_2$HPO$_4$2H$_2$O (mg/g) | NaH$_2$PO$_4$H$_2$O (mg/g) | RhFSH | Pluronic F68 (µg/g) | TWEEN (µg/g) | Ascorbic Acid (µg/g) | Methionine (µg/g) | Bacteriostat | Excipient |
|---|---|---|---|---|---|---|---|---|---|
| 60 | 1.11 | 0.45 | 600 IU/g | 100 | — | 100 | — | 0.9% benzyl alcohol | Mannitol |
| 61 | 1.11 | 0.45 | 600 IU/g | 100 | — | — | — | Phenol | Sucrose |
| 62 | 1.11 | 0.45 | 600 IU/g | 100 | — | — | — | Phenol | Mannitol |
| 63 | 1.11 | 0.45 | 600 IU/g | | | | | Phenol | Sucrose |
| 64 | 1.11 | 0.45 | 600 IU/g | 100 | — | — | 10 | Phenol | Mannitol |
| 65 | 1.11 | 0.45 | 600 IU/g | 100 | — | — | 100 | Phenol | Sucrose |
| 66 | 1.11 | 0.45 | 600 IU/g | 100 | — | — | 100 | Phenol | Mannitol |
| 67 | 1.11 | 0.45 | 600 IU/g | 100 | — | 10 | — | Phenol | Sucrose |
| 68 | 1.11 | 0.45 | 600 IU/g | 100 | — | 10 | — | Phenol | Mannitol |
| 69 | 1.11 | 0.45 | 600 IU/g | 100 | — | 100 | — | Phenol | Sucrose |
| 70 | 1.11 | 0.45 | 600 IU/g | 100 | — | 100 | — | Phenol | Mannitol |

FSH was added to the formulations on the basis of its biopotency instead of protein content.

20 g of each formulation was prepared into Falcon polypropylene tubes and filtered through a 3 cm$^2$ 0.22 µm Millex-GV Syringe Driven filter unit Durapore, then analysed for a value at t=0. The solutions were then stored at 40° C. and tested according the following scheme:

| Analytical test | T = 0 | 1 week | 2 weeks | 3 weeks | 4 weeks |
|---|---|---|---|---|---|
| Reverse Phase-HPLC for oxidised alpha subunit (%) | X | X | X | X | X |
| Size Exclusion-HPLC for protein quantitation (µg/g) | X | X | X | X | X |
| Size Exclusion-HPLC for qualitative free subunits | X | X | X | X | X |

X: Test performed

Reverse phase HPLC reveals that in formulations containing FSH, Pluronic F68, m-cresol and methionine (at 10 and 100 µg/ml), oxidation of the α-subunit of FSH when the formulation is stored at 40° C., is greatly reduced, versus a formulation containing no methionine, as can be seen in FIG. 1. Based on the average of two experiments, in the Formulation containing no methionine, the percent of oxidised α-subunit is 2.3 at T=0, 4.0 at T=1 week and 7.1 at T=2 weeks. In the formulation containing 10 µg/ml methionine, the percent of oxidised α-subunit is 2.0 at T=0, 3.2 at T=1 week and 3.8 at T=2 weeks. In the formulation containing 100 µg/ml methionine, the percent of oxidised α-subunit is 1.8 at T=0, 1.7 at T=1 week, and 1.3 at T=2 weeks.

Example 2

Liquid Single-Dose Formulation of Recombinant FSH for Subcutaneous or Intramuscular Injection Based on the results of Example 1, the following formulation was prepared.

Components 1 to 7 listed in Table 3 were prepared as volumetric solutions in WFI. Aliquots of each solution were added to a mixing vessel to form a "mother solution". The mother solution was dispensed into vials to contain 10.9 micrograms (150 IU) or 5.45 micrograms (75 IU) of FSH.

With recombinant FSH, the bioactivity and specific activity are consistent, allowing the FSH to be filled by mass, rather than by bioassay.

TABLE 3

Components of FSH single dose liquid formulations

| Component # | Description | 150 IU FSH | 75 IU FSH |
|---|---|---|---|
| 1 | rhFSH (µg/vial) | 10.9 (150 IU) | 5.45 (75 IU) |
| 2 | Sucrose (mg/vial) | 15.00 | 7.50 |
| 3 | NaH$_2$PO$_4$.H$_2$O (mg/vial) | 0.111 | 0.0555 |
| 4 | Na$_2$HPO$_4$.2H$_2$O (mg/vial) | 0.273 | 0.1365 |
| 5 | Pluronic F68 (mg/vial) | 0.025 | 0.0125 |
| 6 | Methionine (mg/vial) | 0.025 | 0.0125 |
| 7 | m-cresol (mg/vial) | 0.75 | 0.375 |
| 8 | PH | 7.0 | 7.0 |
| 9 | WFI | q.s. to 1 ml | q.s. to 0.5 ml |

The vials were filled and sealed under sterile conditions. The formulation has a shelf life of up to two years at ambient temperatures.

Example 3

Liquid Multi-Dose Formulation of Recombinant FSH for Subcutaneous or Intramuscular Injection Based on the results of Example 1, the following multi-dose formulation was prepared.

Components 1 to 7 listed in Table 4 were prepared as volumetric solutions in WFI. Aliquots of each solution were added to a mixing vessel to form a "mother solution". The mother solution was dispensed into vials to contain 22.2 micrograms (305 IU), 33.3 micrograms (458 IU) and 66.7 micrograms (916 IU) of FSH. The resulting formulations deliver a total of 300, 450 and 900 IU of FSH.

The cartridges were filled and sealed under sterile conditions. The multi-dose formulation can be stored at or about 2-8° C., more preferably at or about 4-5° C., until the first use for up to two years. After the first use, the cartridge should be stored at or about 2-8° C., more preferably at or about 4-5° C., over the multi-dose period, which may be 24 hours, 2 days, or up to 12 or 14 days.

TABLE 4

Components of FSH multi-dose liquid formulations

| Component # | Description | 300 IU FSH | 450 IU FSH | 900 IU FSH |
|---|---|---|---|---|
| 1 | rhFSH (µg/cartridge) | 22.2 (305 IU) | 33.3 (458 IU) | 66.7 (916 IU) |
| 2 | Sucrose (mg/cartridge) | 30.0 | 45.0 | 90.0 |
| 3 | $NaH_2PO_4 \cdot H_2O$ (mg/cartridge) | 0.225 | 0.337 | 0.675 |
| 4 | $Na_2HPO_4 \cdot 2H_2O$ (mg/cartridge) | 0.555 | 0.832 | 1.665 |
| 5 | Pluronic F68 (mg/vial) | 0.050 | 0.075 | 0.150 |
| 6 | Methionine (mg/vial) | 0.050 | 0.075 | 0.150 |
| 7 | m-cresol (mg/vial) | 1.50 | 2.25 | 4.50 |
| 8 | pH | 7.0 | 7.0 | 7.0 |
| 9 | WFI | q.s. to 0.5 ml | q.s. to 0.75 ml | q.s. to 1.5 ml |

Example 4

Liquid Single-Dose Formulation of Recombinant LH for Subcutaneous or Intramuscular Injection The following formulation was prepared.

Components 1 to 7 listed in Table 5 were prepared as volumetric solutions in WFI. Aliquots of each solution were added to a mixing vessel to form a "mother solution". The mother solution was dispensed into vials to contain 3 micrograms (75 IU) of LH. The resulting formulation delivers a single dose of 75 IU LH.

With recombinant LH, the bioactivity and specific activity are consistent, allowing the LH to be filled by mass, rather than by bioassay.

TABLE 5

Components of LH single dose liquid formulation

| Component # | Description | LH 75 IU |
|---|---|---|
| 1 | rhLH (µg/vial) | 3.0 |
| 2 | Sucrose (mg/vial) | 52.5 |
| 3 | $NaH_2PO_4 \cdot H_2O$ (mg/vial) | 0.052 |
| 4 | $Na_2HPO_4 \cdot 2H_2O$ (mg/vial) | 0.825 |
| 5 | Pluronic F68 (mg/vial) | 0.0125 |
| 6 | Methionine (mg/vial) | 0.125 |
| 7 | m-cresol (mg/vial) | 0.375 |
| 9 | WFI | q.s. to 0.5 ml |

The vials were filled and sealed under sterile conditions. The formulation has a shelf life of up to two years.

Example 5

Liquid Multi-Dose Formulations of Recombinant FSH and LH (2:1) for Subcutaneous or Intramuscular Injection The following multi-dose formulations of FSH and LH were prepared with FSH:LH ratio of 2:1.

Components 1 to 8 listed in Table 6 were prepared as volumetric solutions in WFI. Aliquots of each solution were added to a mixing vessel and mixed to form a "mother solution". The pH of the mother solution was adjusted to 8.0, if necessary, by addition of NaOH or HCl. The mother solution was dispensed into cartridges to contain 18.3 micrograms LH (457 IU) with 66.7 micrograms FSH (916 IU), intended for 6 doses of 150 IU FSH each; 9.2 micrograms LH (230 IU) with 33.3 micrograms FSH (458 IU), intended for 3 doses of 150 IU FSH each; and 6.1 micrograms LH (152.5 IU) with 2223 micrograms FSH (305 IU), intended for 2 doses of 150 IU FSH each.

The cartridges were filled and sealed under sterile conditions. The multi-dose formulation can be stored at or about 2-8° C., more preferably at or about 4-5° C. until the first use for up to two years. After the first use, the cartridge should be stored at at or about 2-8° C., more preferably at or about 4-5° C., over the multi-dose period, which may be 24 hours, 2 days, or up to 12 or 14 days.

TABLE 6

Components of FSH and LH (2:1) multi-dose liquid formulations

| Component # | Description | 6 doses | 3 doses | 2 doses |
|---|---|---|---|---|
| 1 | rhLH (µg/cartridge) | 18.3 (457 IU) | 9.2 (230 IU) | 6.1 (152.5 IU) |
| 2 | rhFSH (µg/cartridge) | 66.7 (916 IU) | 33.3 (458 IU) | 22.23 (305 IU) |
| 3 | Sucrose (mg/cartridge) | 115.5 | 57.75 | 38.5 |
| 4 | $H_3PO_4$ (mg/cartridge) | 1.35 | 0.735 | 0.49 |
| 5 | NaOH (mg/cartridge) | q.s. to pH 8.0 | q.s. to pH 8.0 | q.s. to pH 8.0 |
| 6 | Pluronic F68 (mg/vial) | 375.0 | 187.5 | 125.0 |

TABLE 6-continued

Components of FSH and LH (2:1) multi-dose liquid formulations

| Component # | Description | 6 doses | 3 doses | 2 doses |
|---|---|---|---|---|
| 7 | Methionine (μg/cartridge) | 225 | 112.5 | 75.0 |
| 8 | m-cresol (mg/cartridge) | 4.5 | 2.25 | 1.5 |
| 9 | pH | 8.0 | 8.0 | 8.0 |
| 10 | WFI | q.s. to 1.5 ml | q.s. to 0.75 ml | q.s. to 0.5 ml |

Example 6

Liquid Multi-Dose Formulations of Recombinant FSH and LH (1:1) for Subcutaneous or Intramuscular Injection The following multi-dose formulations of FSH and LH were prepared, with FSH:LH ratio of 1:1.

Components 1 to 8 listed in Table 7 were prepared as volumetric solutions in WFI. Aliquots of each solution were added to a mixing vessel and mixed to form a "mother solution". The pH of the mother solution was adjusted to 8.0, if necessary, by addition of NaOH or HCl. The mother solution was dispensed into cartridges to contain 36.6 micrograms LH (914 IU) with 66.7 micrograms FSH (916 IU), intended for 6 doses of 150 IU FSH each; 18.4 micrograms LH (460 IU) with 33.3 micrograms FSH (458 IU), intended for 3 doses of 150 IU FSH each; and 122 micrograms LH (305 IU) with 22.23 micrograms FSH (305 IU), intended for 2 doses of 150 IU FSH each.

The cartridges were filled and sealed under sterile conditions. The multi-dose formulation can be stored at or about 2-8° C., more preferably at or about 4-5° C. until the first use for up to two years. After the first use, the cartridge should be stored at or about 2-8° C., more preferably at or about 2-8° C., more preferably at or about 4-5° C., over the multi-dose period, which may be 24 hours, 2 days, or up to 12 or 14 days.

Example 7

Stability Experiments for Liquid Multi-Dose Formulations of FSH Mixed with LH 7.1. Reverse Phase HPLC Analysis for Protein Content The formulation of Example 5 (6 doses) was evaluated for protein content for both FSH and LH, using a reverse-phase HPLC method.

Protein content (FSH and LH) was measured at zero time, and after 1, 2, 3 and 6 months storage of the formulation at 4° C. The results are listed in Table 8 as micrograms of FSH or LH per gram of solvent.

7.2. Assay of Oxidised Alpha-Subunit

The percentage of oxidised alpha-subunit in a formulation of Example 5 was measured by a reverse phase HPLC (RP-HPLC) method.

The percentage of oxidised alpha-subunit was measured at zero time, and after 1, 2, 3 and 6 months storage at 4° C. The results are listed in Table 8.

7.3. In Vivo Assay for FSH

The formulation of Example 5 (6 doses) was tested for FSH activity using the Steelman-Pohley ovarian weight gain bioassay at zero time, and after 1, 2, 3 and 6 months of storage at 4° C. The results are listed in Table 8 as international units (IU) per gram of solvent

TABLE 7

Components of FSH and LH (1:1) multi-dose liquid formulations

| Component # | Description | 6 doses | 3 doses | 2 doses |
|---|---|---|---|---|
| 1 | rhLH (μg/cartridge) | 36.6 (914 IU) | 18.4 (460 IU) | 12.2 (305 IU) |
| 2 | rhFSH (μg/cartridge) | 66.7 (916 IU) | 33.3 (458 IU) | 22.23 (305 IU) |
| 3 | Sucrose (mg/cartridge) | 115.5 | 57.75 | 38.5 |
| 4 | $H_3PO_4$ (mg/cartridge) | 1.35 | 0.735 | 0.49 |
| 5 | NaOH (mg/cartridge) | q.s. to pH 8.0 | q.s. to pH 8.0 | q.s. to pH 8.0 |
| 6 | Pluronic F68 (mg/vial) | 375.0 | 187.5 | 125.0 |
| 7 | Methionine (μg/cartridge) | 225 | 112.5 | 75.0 |
| 8 | m-cresol (mg/cartridge) | 4.5 | 2.25 | 1.5 |
| 9 | pH | 8.0 | 8.0 | 8.0 |
| 10 | WFI | q.s. to 1.5 ml | q.s. to 0.75 ml | q.s. to 0.5 ml |

7.4. In Vivo Assay for LH

The formulation of Example 5 (6 doses) was tested for LH activity using the rat seminal vesicle weight gain bioassay at zero time, and after 1, 2, 3 and 6 months of storage at 4° C. The results are listed in Table 8 as international units (IU) per gram of solvent.

7.5. Evaluation of Free Subunit (rFSH+rLH)

For a formulation of Example 5 the percentage of free subunit was evaluated by SDS-PAGE.

Measurements were made at zero time, and after 1, 2, 3 and 6 months storage at 4° C. The results are reported as a percentage of the total protein (rFSH+rLH), and are listed in Table 8.

7.5. Evaluation of Aggregates

For a formulation of Example 5, the percentage of aggregates was evaluated by SDS-PAGE as described above for evaluation of free subunit in 7.5, except that higher molecular weight aggregates were determined as a percentage of the total protein (rFSH+rLH). Measurements were made at zero time and after 1, 2, 3 and 6 months storage at 4° C. Results are listed in Table 8.

7.6. Visible Particles

The formulation of Example 5 was evaluated visually for particles at zero time, and after 3 and 6 months of storage at 4° C. Results are reported in Table 8.

7.7. pH

The pH of a formulation of Example 5 was measured at zero time and after 1, 2, 3 and 6 months storage at 4° C. Results are listed in Table 8.

| Formulation A | |
|---|---|
| FSH | μg 32.75 (450 I.U.) |
| LH | μg 9.0 (225 I.U.) |
| Sucrose | mg 15.0 |
| $NaH_2PO_4H_2O$ | mg 0.052 |
| $Na_2HPO_42H_2O$ | mg 0.825 |
| Pluronic F-68 | mg 0.05 |
| L-Methionine | mg 0.05 |

| Formulation B | |
|---|---|
| FSH | μg 65.5 (900 I.U.) |
| LH | μg 18.0 (450 I.U.) |
| Sucrose | mg 30.0 |
| $NaH_2PO_4H_2O$ | mg 0.104 |
| $Na_2HPO_42H_2O$ | mg 1.65 |
| Pluronic F68 | mg 0.10 |
| L-Methionine | mg 0.10 |

The manufacturing process consists in mixing the drug substance directly with the ingredients, filtrating the solution obtained and lyophilising the filtrated.

A description of each step of the process is given in the following:

add in a tared container WFI, di-sodium hydrogen phosphate dihydrate, sodium dihydrogen phosphate mono-

TABLE 8

Analytical parameters for a liquid formulation of FSH and LH (2:1) at zero time and after storage at 4° C. for 1, 2, 3 and 6 months

| Assay | Zero time | 1 month | 2 months | 3 months | 6 months |
|---|---|---|---|---|---|
| rFSH content by RP-HPLC (micrograms/g) | 46.50 | 46.98 | 46.71 | 46.31 | 44.98 |
| rLH content by RP-HPLC (micrograms/g) | 11.74 | 11.81 | 12.68 | 12.67 | 13.21 |
| % alpha-subunit oxidised | 2.29 | 2.17 | 2.08 | 2.48 | 2.95 |
| In vivo assay for FSH 553(IU/g) | 566 | Not tested | Not tested | Not tested | 578 (23 weeks) |
| In vivo assay for LH (IU/g) | 331 | Not tested | Not tested | 311 | 286 |
| SDS-PAGE free subunit (rFSH + rLH; %) | ≦5 | Not tested | Not tested | ≦5 | ≦5 (23 weeks) |
| SDS-PAGE aggregates (rFSH + rLH; %) | ≦2 | Not tested | Not tested | >3 | 4 |
| Visible particles | Free | Not tested | Not tested | Free | Free |
| pH | 8.262 | 8.215 | 8.216 | 8.188 | 8.283 |

Example 8

FSH and LH Freeze Dried Multidose Formulation

Two freeze dried formulations A and B having the following compositions have been prepared:

hydrate, Sucrose, Pluronic F68 at 5% and L-methionine and stir for 10 minutes until complete dissolution.

check the pH and eventually correct it to pH 7.00±0.2 with NaOH 10% or diluted $H_3PO_4$ add FSH and LH to the above prepared mixture and gently stir the solution obtained for 10 minutes.

check the pH again and eventually adjust it to 7.0±0.1 with 10% NaOH or diluted $H_3PO_4$.

filter the solution with a 0.22 μm Durapore membrane with a filtration ratio not less than 15 g/cm2 under Nitrogen gas flow with a pressure not higher than 1.5 atm.

collect the solution in a previously sterilised flask.

fill the filtered solution into the glass container, seat the stopper and place the filled vials into a stainless steel tray.

load the trays into the freeze dryer and lyophilise the product using the following freeze drying cycle:

equilibrate at +4° C. for about 20 mins.

bring the shelves temperature at −25° C. and maintain for 2 hours.

bring the shelves temperature at −15° C. and maintain for 1 hour.

bring the shelves temperature at −45° C. and maintain for 3 hours.

bring condenser temperature at −65° C.

apply vacuum to the chamber.

When the vacuum reaches a value of $7 \times 10^{-2}$ mBar raise shelf temperature up to −10° C. and maintain for 14 hours.

raise the shelf temperature up to +35° C. in 8 hours and maintain up to the end of the cycle (14 hours).

break the vacuum allowing dry nitrogen into the chamber.

perform the stoppering by automatic system of the freeze dryer.

seal the stoppered vials with the appropriate flip-off caps.

The formulations A and B have been stored at 25±2° C., and tested for stability and biological activity as pointed out below. Prior to analysing the compositions, they are reconstituted using water for injection comprising 0.3% of m-Cresol as bacteriostatic agent.

The stability and biological activity values were determined as follows:

In vivo assay for FSH: The formulation was tested for FSH activity using the Steelman-Pohley ovarian weight gain bioassay In vivo assay for LH: The formulation was tested for LH activity using the rat seminal vesicle weight gain bioassay.

Assay of oxidised alpha-subunit: The percentage of oxidised alpha-subunit was measured by a reverse phase HPLC (RP-HPLC) method.

Evaluation of free subunit (rFSH+rLH): The percentage of free subunit was evaluated by SDS-PAGE.

Evaluation of aggregates: The percentage of aggregates was evaluated by SDS-PAGE as described above for evaluation of free subunit.

The biological tests have been performed in compliance with the regulations of the European Pharmacopeia. In particular the tests are reported in the "Menotropin" monography.

Table 9 summarizes the results of the analytical tests related to stability and biological activity of formulation A. The values were determined at 4 check-points: at time zero, after 1 month, 3 months and 6 months of storage, at a storage temperature of 25±2° C.

TABLE 9

| TEST | TIME ZERO | 1 MONTHS | 3 MONTHS | 6 MONTHS |
|---|---|---|---|---|
| Biological activity I.U. FSH | 416 | 420 | 415 | 417 |
| Biological activity I.U. LH | 276 | 250 | 259 | 270 |
| % oxidised product | 1.95 | 1.81 | 1.95 | 1.57 |
| % dimers/aggregates | <2 | <2 | <2 | <2 |
| % free subunits | <5 | <5 | <5 | <5 |

Table 10 summarizes the results of the analytical tests related to stability and biological activity of formulation B. The values were determined at 4 check-points: at time zero, after 3 month, 6 months and 9 months of storage, at a storage temperature of 25±2° C.

TABLE 10

| TEST | TIME ZERO | 3 MONTHS | 6 MONTHS | 9 MONTHS |
|---|---|---|---|---|
| Biological activity I.U. FSH | 821 | 850 | 830 | 838 |
| Biological activity I.U. LH | 570 | 564 | 580 | 622 |
| % oxidised product | 1.0 | 0.9 | 1.0 | 1.0 |
| % dimers/aggregates | <2 | <2 | <2 | <2 |
| % free subunits | <5 | <5 | <5 | <5 |

From TABLE 9 and 10 it may be concluded that the biological activity of formulations A and B is well conserved after 9 months of storage. The formulations have a high stability.

The high stability is not affected by large amounts of recombinant FSH and recombinant LH.

Sequences:

SEQ ID NO. 1: human glycoprotein α-subunit

SEQ ID NO. 2: hFSH β-subunit

SEQ ID NO. 3: hFSH β-subunit variant 1

SEQ ID NO. 4: hFSH β-subunit variant 2

SEQ ID NO. 5: hFSH β-subunit variant 3

SEQ ID NO. 6: hLH β-subunit

REFERENCES

[1] Burgues et al.: *Subcutaneous self-administration of highly purified follicle stimulating hormone end human chorionic gonadotrophin for the treatment of male hypogonadotrophic hypogonadism. Spanish Collaborative Group on Male Hypogonadotrophic Hypogonadism; Hum. Reprod.;* 1997, 12, 980-6;

[2] Shome et al., J. Clin. Endocrinol. Meteb. 39:187-205 (1974); Shome, et al., J. Prot. Chem, 7:325-339, 1988;

[3] Keutmann et al.; *Structure of human luteinizing hormone beta subunit: evidence for related carboxyl-terminal sequence among certain peptide hormones; Biochem. Biophys. Res. Commun.;* 1979, 90, 842-848; Talmadge et al.; *Evolution of the genes for the beta subunits of human chorionic gonadotropin and luteinizing hormone; Nature;* 1984, 307, 37-40; Fiddes & Talmadge; *Structure, expression, and evolution of the genes for the human glycoprotein hormones; Recent Prog. Horm. Res.;* 1984, 40, 43-78

[4] Reichert L E, Ramsey R B; Dissociation of human follicle-stimulating hormone; J. Biol. Chem.; 1975, 250, 3034-3040

[5] Klein et al.; *Pharmacokinetics and pharmacodynamics of single-chain recombinant human follicle-stimulating hormone containing the human chorionic gonadotrophin carboxyterminal peptide in the rhesus monkey; Fertility & Sterility;* 2602, 77, 1248-1255

[6] a) Fiddes, J. C., et al., J of Mol. and Applied Genetics, 1:3-18(1981); b) Esch F. S., et al. DNA 5:363-389(1986); c) Watkins P. C., et al., DNA 6:205-212(1987); d) Hirai T., et al., J. Mol. Endrocrinol. 5:147-158(1990); e) Maurer, R. A., et al., Mol. Endocrinol. 1:717-723(1987); f) Guzman K., et al., DNA Cell Biol. 10:593-601(1991); g) Kumar T R, et al., Gene. 1995 Dec. 12; 166(2):335-6; h) Kumar T R, et al., Gene. 1995 Dec. 12; 166(2):333-4

[7] Biochem. Biophys. Res. Commun.; 1979, 90, 842-848

[8] Steelman et al.; Assay of the follicle stimulating hormone based on the augmentation with human chorionic gonadotrophin; Endocrinology, 1953, 53, 604-616

[9] Van Hell et al.; *Effects of human menopausal gonadotrophin preparations in different bioassay methods; Acta Endocrinologica;* 1964, 47, 409-418

[10] Van Hell et al.; *Effects of human menopausal gonadotrophin preparations in different bioassay methods; Acta Endocrinologica;* 1964, 47, 409-418

---

The invention claimed is:

1. A liquid pharmaceutical composition, comprising:
   a follicle stimulating hormone,
   m-cresol,
   a diluent, and
   poloxamer 188,
   the composition having a stability sufficient to avoid precipitation.

2. The composition according to claim 1, wherein the follicle stimulating hormone is present in an amount of from 150 IU/ml to 1200 IU/ml.

3. The composition according to claim 1, wherein the follicle stimulating hormone is present in an amount of from 300 IU/ml to 900 IU/ml.

4. The composition according to claim 1, wherein the follicle stimulating hormone is present in an amount of about 600 IU/ml.

5. The composition according to claim 1, wherein the follicle stimulating hormone is human follicle stimulating hormone.

6. The pharmaceutical composition according to claim 1, wherein the follicle stimulating hormone is urinary human follicle stimulating hormone.

7. The composition according to claim 1, wherein the follicle stimulating hormone is recombinant human follicle stimulating hormone.

8. The composition according to claim 1, further comprising sucrose.

9. The composition according to claim 1, further comprising methionine.

10. The composition according to claim 1, further comprising a phosphate buffer, wherein the pH of the composition is from 6.0 to 8.0.

11. The composition according to claim 1, further comprising a phosphate buffer, wherein the pH of the composition is about 7.0.

12. The composition according to claim 1, comprising the diluent, recombinant follicle stimulating hormone, poloxamer 188, sucrose, methionine, m-cresol, and an aqueous buffer, and wherein the pH of the composition is about 7.0.

13. The composition according to claim 12, wherein the recombinant follicle stimulating hormone is present in an amount of about 600 IU/ml, the poloxamer 188 is present in an amount of about 0.1 mg/ml, the sucrose is present in an amount of about 60 mg/ml, the methionine is present in an amount of about 0.1 mg/ml, the m-cresol is present in an amount of about 3 mg/ml, and the phosphate buffer is present in an amount of about 10 mM in phosphate.

14. The composition according to claim 1, wherein the diluent is water for injection.

15. A liquid pharmaceutical composition, comprising:
   a follicle stimulating hormone,
   a luteinising hormone,
   a bacteriostatic agent selected form the group consisting of phenol and m-cresol,
   poloxamer 188, and
   a diluent
   wherein either the follicle stimulating hormone is human follicle stimulating hormone, or the luteinising hormone is human luteinising hormone, or both the follicle stimulating hormone is human follicle stimulating hormone and the luteinising hormone is human luteinising hormone, the composition having a stability sufficient to avoid precipitation.

16. A liquid pharmaceutical composition, comprising:
a follicle stimulating hormone,
a luteinising hormone,
a bacteriostatic agent selected form the group consisting of phenol and m-cresol,
poloxamer 188, and
a diluent
wherein either the follicle stimulating hormone is urinary human follicle stimulating hormone, or the luteinising hormone is urinary human luteinising hormone, or both the follicle stimulating hormone is urinary human follicle stimulating hormone and the luteinising hormone is urinary human luteinising hormone,
the composition having a stability sufficient to avoid precipitation.

17. A liquid pharmaceutical composition, comprising:
a follicle stimulating hormone,
a luteinising hormone,
a bacteriostatic agent selected form the group consisting of phenol and m-cresol,
poloxamer 188, and
a diluent
wherein either the follicle stimulating hormone is recombinant human follicle stimulating hormone, or the luteinising hormone is recombinant human luteinising hormone, or both the follicle stimulating hormone is recombinant human follicle stimulating hormone and the recombinant luteinising hormone is human luteinising hormone,
the composition having a stability sufficient to avoid precipitation.

18. The composition according to claim 15, wherein the follicle stimulating hormone and the luteinising hormone are present in a ratio of from 6:1 to 1:6.

19. The composition according to claim 15, wherein the follicle stimulating hormone and the luteinising hormone are present in a ratio of from 4:1 to 1:2.

20. The composition according to claim 15, wherein the follicle stimulating hormone and the luteinising hormone are present in a ratio of from 3:1 to 1:1.

21. The composition according to claim 15, wherein the follicle stimulating hormone and the luteinising hormone are present in a ratio of from 2:1 to 1:1.

22. The composition according to claim 15, in which the bacteriostatic agent is phenol.

23. The composition according to claim 15, in which the bacteriostatic agent is m-cresol.

24. The composition according to claim 15, further comprising sucrose.

25. The composition according to claim 15, further comprising methionine.

26. The composition according to claim 15, further comprising a phosphate buffer, wherein the pH of the composition is from 6.0 to 8.0.

27. The composition according to claim 15, further comprising a phosphate buffer, wherein the pH of the composition is about 7.0.

28. The composition according to claim 15, comprising the diluent, recombinant follicle stimulating hormone, luteinising hormone, poloxamer 188, sucrose, methionine, phenol, and an aqueous buffer, wherein the pH of the composition is about 7.0.

29. The composition according to claim 28, wherein the recombinant follicle stimulating hormone is present in an amount of about 600 IU/ml, the poloxamer 188 is present in an amount of about 0.1 mg/ml, the sucrose is present in an amount of about 60 mg/ml, the methionine is present in an amount of about 0.1 mg/ml, the phenol is present in an amount of about 3 mg/ml, and the buffer is a phosphate buffer present in an amount of about 10 mM in phosphate.

30. The composition according to claim 15, wherein the diluent is water for injection.

31. The composition according to claim 15, wherein the diluent is at least one of water and a mixture of water and a solvent miscible with water.

32. The composition according to claim 15, wherein the follicle stimulating hormone is present in an amount of from 150 IU/ml to 1200 IU/ml.

33. The composition according to claim 15, wherein the follicle stimulating hormone is present in an amount of from 300 IU/ml to 900 IU/ml.

34. The composition according to claim 15, wherein the follicle stimulating hormone is present in an amount of about 600 IU/ml.

35. The composition according to claim 15, wherein the luteinising hormone is present in an amount of from 150 IU/ml to 1200 IU/ml.

36. The composition according to claim 15, wherein the luteinising hormone is present in an amount of from 300 IU/ml to 750 IU/ml.

37. The composition according to claim 28, wherein the luteinising hormone is recombinant luteinising hormone.

38. The composition according to claim 37, wherein the follicle stimulating hormone and the luteinising hormone are present in a ratio of from 2:1.

39. The composition according to claim 38, wherein the buffer is a phosphate buffer.

40. A liquid pharmaceutical composition, comprising:
a follicle stimulating hormone,
phenol,
a diluent, and
poloxamer 188,
the composition having a stability sufficient to avoid precipitation.

41. The composition according to claim 40, wherein the follicle stimulating hormone is present in an amount of from 150 IU/ml to 1200 IU/ml.

42. The composition according to claim 40, wherein the follicle stimulating hormone is present in an amount of from 300 IU/ml to 900 IU/ml.

43. The composition according to claim 40, wherein the follicle stimulating hormone is present in an amount of about 600 IU/ml.

44. The composition according to claim 40, wherein the follicle stimulating hormone is human follicle stimulating hormone.

45. The pharmaceutical composition according to claim 40, wherein the follicle stimulating hormone is urinary human follicle stimulating hormone.

46. The composition according to claim 40, wherein the follicle stimulating hormone is recombinant human follicle stimulating hormone.

47. The composition according to claim 40, further comprising sucrose.

48. The composition according to claim 40, further comprising methionine.

49. The composition according to claim 40, further comprising a phosphate buffer, wherein the pH of the composition is from 6.0 to 8.0.

50. The composition according to claim 40, further comprising a phosphate buffer, wherein the pH of the composition is about 7.0.

51. The composition according to claim 40, wherein the diluent is water for injection.

52. The composition according to claim 40, wherein the diluent is at least one of water and a mixture of water with a solvent miscible with water.

53. The composition according to claim 1 consisting essentially of recombinant follicle stimulating hormone, m-cresol, diluent, poloxamer 188, sucrose, methionine, and phosphate buffer.

54. The composition according to claim 53, wherein the recombinant follicle stimulating hormone is present in an amount of about 600 IU/ml, the m-cresol is present in an amount of about 3 mg/ml, the poloxamer 188 is present in an amount of about 0.1 mg/ml, the sucrose is present in an amount of about 60 mg/ml, the methionine is present in an amount of about 0.1 mg/ml, and the phosphate buffer is present in an amount of about 10 mM in phosphate.

55. The composition according to claim 15 consisting essentially of the diluent, recombinant follicle stimulating hormone, recombinant luteinising hormone, phenol, diluent, poloxamer 188, sucrose, methionine, and phosphate buffer.

56. The composition according to claim 55, wherein the recombinant follicle stimulating hormone is present in an amount of about 600 IU/ml, the recombinant luteinising hormone is present in an amount of about 300 IU/ml, the poloxamer 188 is present in an amount of about 0.25 mg/ml, the sucrose is present in an amount of about 77 mg/ml, and the methionine is present in an amount of about 0.15 mg/ml.

57. The composition according to claim 40, comprising the diluent, recombinant follicle stimulating hormone, phenol, poloxamer 188, sucrose, methionine, and an aqueous buffer, and wherein the pH of the composition is about 7.0.

58. The composition according to claim 40 consisting essentially of the diluent, recombinant follicle stimulating hormone, phenol, poloxamer 188, sucrose, methionine, and an aqueous buffer, and wherein the pH of the composition is about 7.0.

* * * * *